United States Patent [19]
Ruegg et al.

[11] Patent Number: 5,646,251
[45] Date of Patent: Jul. 8, 1997

[54] ALLOREACTION-ASSOCIATED ANTIGEN (ARAG): A NOVEL MEMBER OF THE IMMUNOGLOBULIN GENE SUPERFAMILY

[75] Inventors: Curtis L. Ruegg, San Carlos; Alberto Rivas, Palo Alto; Reiner Laus, Belmont; Edgar G. Engleman, Atherton, all of Calif.

[73] Assignee: The Board of Trustees of Leeland Stanford Jr. Univ., Palo Alto, Calif.

[21] Appl. No.: 497,025

[22] Filed: Jun. 30, 1995

Related U.S. Application Data

[63] Continuation-in-part of Ser. No. 149,212, Nov. 5, 1993, abandoned.

[51] Int. Cl.⁶ .................. C07K 7/00; C07K 14/705; C12N 15/00
[52] U.S. Cl. .................. 530/350; 530/324; 530/325; 530/326; 530/395; 435/69.1; 435/172.3
[58] Field of Search .................. 530/324, 325, 530/326, 350, 395; 435/69.1, 172.3

[56] References Cited

FOREIGN PATENT DOCUMENTS

| | | | |
|---|---|---|---|
| 9004641A | 5/1990 | WIPO . | |
| 15076 | 12/1990 | WIPO | C07K 15/28 |
| 11870 | 7/1992 | WIPO | A61K 39/395 |

OTHER PUBLICATIONS

Halfter et al. 1989. EMBO J. 8: 4265–72.
Compton et al. Mar. 1992. J. Cell Biol. 116: 1395–1408.
Aruffo et al., "Molecular cloning of a CD28 cDNA by a high–efficiency COS cell expression system," *Proc. Natl. Acad. Sci. USA* 84:8573–8577 (1987).
Kallunki et al., "Human basement membrane heparan sulfate proteoglycan core protein: a 467–kD protein containing multiple domains resembling elements of the low density lipoprotein receptor, laminin, neural cell adhesion molecules, and epidermal growth factor," *J. Cell Biol* 116:559–571 (1992).

Mackay et al., "Cell adhesion in the immune system," *Immunology Today* 14:99–102 (1993).

Triebel et al., "LAG–3, a novel lymphocyte activation gene closely related to CD4," *J. Exp. Med.* 171:1393–1405 (1990).

Wadsworth et al., "Developmentally regulated expression of the $\beta_4$ integrin on immature mouse thymocytes" *J. Immunol.* 149:421–428 (1992).

Wang et al., "Identification and molecular cloning of tactile. A novel human T cell activation antigen that is a member of the Ig gene superfamily," *J. Immunol.* 148:2600–2608 (1992).

Williams et al., "The immunoglobulin superfamily–domains for cell surface recognition," *Ann. Rev. Immunol.* 6:381–405 (1988).

*Primary Examiner*—Stephen G. Walsh
*Assistant Examiner*—Elizabeth C. Kemmerer
*Attorney, Agent, or Firm*—Townsend and Townsend and Crew LLP

[57] ABSTRACT

The invention provides purified ARAg polypeptides, antibodies against ARAg polypeptides and nucleic acids encoding ARAg polypeptides. Also provided are methods of diagnosis and treatment using the same. ARAg polypeptides are typically present on the surface of alloantigen-activated CD8⁺ T-cells, monocytes, granulocytes and peripheral dendritic cells, and substantially absent on resting T-cells, mitogen-activated CD8⁺ T-cells, B-cells, erythroid cell lines, myelomonocitic cell lines, EBV-LCL cell lines and fibroblastoid cell lines. An exemplary ARAg polypeptide, termed ARAg-h-1, has a signal sequence, seven variable-type immunoglobulin-like domains, a transmembrane domain and an intracellular domain.

14 Claims, 12 Drawing Sheets

```
  1 ctctaaagctttagagcccaaatggcaggcatctcatatgtggcatctttctttctcctt   60
  1                       M  A  G  I  S  Y  V  A  S  F  F  L  L   13

61 ctgactaagctcagcattggccagagagaagtaacagttcagaaaggaccactgtttaga  120
 14  L  T  K  L  S  I  G  Q  R  E  V  T  V  Q  K  G  P  L  F  R   33

121 gctgaaggttacccagtcagcattggctgcaatgtaactggccaccagggaccttctgag  180
 34  A  E  G  Y  P  V  S  I  G  C  N  V  T  G  H  Q  G  P  S  E   53
                                    I Δ

181 cagcatttccagtggtctgtttacctgccgacaaacccgacccaggaagtccagatcatt  240
 54  Q  H  F  Q  W  S  V  Y  L  P  T  N  P  T  Q  E  V  Q  I  I   73

241 agcaccaaggatgctgccttctcttacgcagtatatacgcagcgggtgcgaggcggagac  300
 74  S  T  K  D  A  A  F  S  Y  A  V  Y  T  Q  R  V  R  G  G  D   93

301 gtctacgtggagagggtccagggcaactcagtcttgttgcacatctcaaaactccagatg  360
 94  V  Y  V  E  R  V  Q  G  N  S  V  L  L  H  I  S  K  L  Q  M  113

361 aaggatgctggcgagtatgagtgtcacacaccaaacactgatgagaattactatggaagt  420
114  K  D  A  G  E  Y  E  C  H  T  P  N  T  D  E  N  Y  Y  G  S  133
                           I Δ

421 tacagagcaaagactaatctaattgttattccagatacccctctctgccaccatgagttct  480
134  Y  R  A  K  T  N  L  I  V  I  P  D  T  L  S  A  T  M  S  S  153

481 cagactctcggtaaggaggaaggtgagccattagccctcacctgtgaggcatccaaagcc  540
154  Q  T  L  G  K  E  E  G  E  P  L  A  L  T  C  E  A  S  K  A  173
                                              II Δ

541 acagcccaacatactcacctctctgtcacctggtacctaacacaggatggaggaggaagc  600
174  T  A  Q  H  T  H  L  S  V  T  W  Y  L  T  Q  D  G  G  G  S  193

601 caagccactgagattatttctctctccaaagattttatattggtccctgggcccttgtat  660
194  Q  A  T  E  I  I  S  L  S  K  D  F  I  L  V  P  G  P  L  Y  213

661 acagagcggtttgcagccagtgacgtacagctcaacaaactgggacccactacattcagg  720
214  T  E  R  F  A  A  S  D  V  Q  L  N  K  L  G  P  T  T  F  R  233

721 ctgtccatagagaggctccagtcctcagatcagggtcagctgttctgtgaggcaacggaa  780
234  L  S  I  E  R  L  Q  S  S  D  Q  G  Q  L  F  C  E  A  T  E  253
                                              II Δ

781 tggattcaggatccagatgaaacttggatgttcatcaccaaaaagcagaccgatcaaacc  840
254  W  I  Q  D  P  D  E  T  W  M  F  I  T  K  K  Q  T  D  Q  T  273

841 actctgaggatccagccagcagtgaaagattttcaagtcaacattacagctgacagcttg  900
274  T  L  R  I  Q  P  A  V  K  D  F  Q  V  N  I  T  A  D  S  L  293

901 tttgctgaagggaaaccccttagaactggtttgcctggttgtaagcagtggccgtgaccca  960
294  F  A  E  G  K  P  L  E  L  V  C  L  V  V  S  S  G  R  D  P  313
                                    III Δ

961 cagcttcaaggcatttggttcttcaatgggactgaaattgctcacattgatgctggtgga 1020
314  Q  L  Q  G  I  W  F  F  N  G  T  E  I  A  H  I  D  A  G  G  333

1021 gtcctgggcctgaagaatgactacaaagagagagcaagtcaaggagagctccagctttca 1080
334  V  L  G  L  K  N  D  Y  K  E  R  A  S  Q  G  E  L  Q  L  S  353

1081 aagttaggccccaaggctttctctctcaagatcttctctctgggcccagaggatgaaggc 1140
354  K  L  G  P  K  A  F  S  L  K  I  F  S  L  G  P  E  D  E  G  373

1141 gcctacagatgtgtggtagcagaggtcatgaaaacacgcacaggttcctggcaggtgctt 1200
374  A  Y  R  C  V  V  A  E  V  M  K  T  R  T  G  S  W  Q  V  L  393
         III Δ

1201 cagagaaagcagtcaccagacagccacgtgcacctgaggaagccagcagcaagaagtgtg 1260
394  Q  R  K  Q  S  P  D  S  H  V  H  L  R  K  P  A  A  R  S  V  413

1261 gtcgtgtctaccaagaacaagcagcaagttgtgtgggaaggagagacactcgcctttctc 1320
414  V  V  S  T  K  N  K  Q  Q  V  V  W  E  G  E  T  L  A  F  L  433
```

FIG. 7A-1

```
1321 tgtaaggctggtggagctgaaagtcccctgtctgtgagctggtggcacatcccacgggac 1380
 434  C   K   A   G   G   A   E   S   P   L   S   V   S   W   W   H   I   P   R   D   453
          Δ IV
1381 cagacacagcccgagtttgtggctggcatggggcaggatggcattgtgcagctgggtgcc 1440
 454  Q   T   Q   P   E   F   V   A   G   M   G   Q   D   G   I   V   Q   L   G   A   473
1441 tcctatggggtacccagttaccatggcaacacaaggctggagaaaatggactgggccacc 1500
 474  S   Y   G   V   P   S   Y   H   G   N   T   R   L   E   K   M   D   W   A   T   493
1501 ttccagctggagatcaccttcactgccatcacagacagtggcacatatgagtgcagagta 1560
 494  F   Q   L   E   I   T   F   T   A   I   T   D   S   G   T   Y   E   C   R   V   513
                                                              IV Δ
1561 tctgagaagtctcggaaccaggccagagatctgagctggactcagaagatttcagttact 1620
 514  S   E   K   S   R   N   Q   A   R   D   L   S   W   T   Q   K   I   S   V   T   533
1621 gtaaagtctctggagtcaagtttacaagttagtctgatgagccgtcagccgcaggtgatg 1680
 534  V   K   S   L   E   S   S   L   Q   V   S   L   M   S   R   Q   P   Q   V   M   553
1681 ttaaccaacacctttgacctgtcctgtgtcgtgagggccggttactctgacctcaaggtg 1740
 554  L   T   N   T   F   D   L   S   C   V   V   R   A   G   Y   S   D   L   K   V   573
          V Δ
1741 ccactcactgtgacgtggcagttccagccagctagctctcacatattccaccagcttatt 1800
 574  P   L   T   V   T   W   Q   F   Q   P   A   S   S   H   I   F   H   Q   L   I   593
1801 cgaatcacccacaatggcactattgaatgggggaatttcctatcccggttccaaaagaag 1860
 594  R   I   T   H   N   G   T   I   E   W   G   N   F   L   S   R   F   Q   K   K   613
1861 acgaaagtgtcgcagtctttatttcgttcacaactcctagtccatgatgccactgaggaa 1920
 614  T   K   V   S   Q   S   L   F   R   S   Q   L   L   V   H   D   A   T   E   E   633
1921 gagacaggagtgtatcagtgtgaagtagaagtttatgacagaaattccctatacaacaac 1980
 634  E   T   G   V   Y   Q   C   E   V   E   V   Y   D   R   N   S   L   Y   N   N   653
                  V Δ
1981 cgccccccgagggcttctgccatctctcacccactgaggatagccgtcactttaccagag 2040
 654  R   P   P   R   A   S   A   I   S   H   P   L   R   I   A   V   T   L   P   E   673
2041 agcaagctaaaagtgaattcaaggagtcaagggcaagagctctccatcaactccaacact 2100
 674  S   K   L   K   V   N   S   R   S   Q   G   Q   E   L   S   I   N   S   N   T   693
2101 gatatagaatgtagcatcttgtcccggtccaatggaaaccttcagttagccattatttgg 2160
 694  D   I   E   C   S   I   L   S   R   S   N   G   N   L   Q   L   A   I   I   W   713
          VI Δ
2161 tatttttctcctgtttccactaatgcctcttggctaaagatcctggagatggaccaaacc 2220
 714  Y   F   S   P   V   S   T   N   A   S   W   L   K   I   L   E   M   D   Q   T   733
2221 aatgttataaaaactggggatgagtttcacacccacagagaaaacaaaaatttcatact 2280
 734  N   V   I   K   T   G   D   E   F   H   T   P   Q   R   Q   K   F   H   T   753
2281 gagaaggtttcccaagacttatttcagctgcacattctgaatgtggaagacagcgatcgg 2340
 754  E   K   V   S   Q   D   L   F   Q   L   H   I   L   N   V   E   D   S   D   R   773
2341 ggcaaatatcactgtgctgtggaggaatggctcctgtctacaaatggcacttggcacaag 2400
 774  G   K   Y   H   C   A   V   E   E   W   L   L   S   T   N   G   T   W   H   K   793
          VI Δ
2401 cttggagaaaagaagtcaggactaacagaattgaaactcaagcccacaggaagtaaggta 2460
 794  L   G   E   K   K   S   G   L   T   E   L   K   L   K   P   T   G   S   K   V   813
2461 cgtgtctccaaagtgtactggaccgaaaatgtgactgagcacagagaagtggccatccgc 2520
 814  R   V   S   K   V   Y   W   T   E   N   V   T   E   H   R   E   V   A   I   R   833
```

FIG. 7A-2

```
2521  tgcagcctggagagtgtaggcagctcagccactctgtactctgtgatgtggtactggaac  2580
 834   C   S   L   E   S   V   G   S   S   A   T   L   Y   S   V   M   W   Y   W   N    853
          Δ VII
2581  agagaaaactctggaagtaaattgctggtgcacttgcaacatgatggcttgctggagtat  2640
 854   R   E   N   S   G   S   K   L   L   V   H   L   Q   H   D   G   L   L   E   Y    873

2641  ggggaagaggggctcaggaggcacctgcactgttaccgttcatcctctacagactttgtc  2700
 874   G   E   E   G   L   R   R   H   L   H   C   Y   R   S   S   T   D   F   V    893
                                                           Δ
2701  ctgaagcttcatcaggtggagatggaggatgcaggaatgtactggtgtagggtggcagag  2760
 894   L   K   L   H   Q   V   E   M   E   D   A   G   M   Y   W   C   R   V   A   E    913
                                                   VII Δ
2761  tggcagctccatggacacccaagcaagtggattaatcaagcatccgatgagtcacagcgg  2820
 914   W   Q   L   H   G   H   P   S   K   W   I   N   Q   A   S   D   E   S   Q   R    933

2821  atggtgctcacggtgctgccttcagagcccacgcttccttccaggatctgctcctcggcc  2880
 934   M   V   L   T   V   L   P   S   E   P   T   L   P   S   R   I   C   S   S   A    953
                                                                   Δ
2881  cctttactctatttcctgttcatctgtcccttcgtcctgctcctccttctgctcatctcc  2940
 954   P   L   L   Y   F   L   F   I   C   P   F   V   L   L   L   L   L   L   I   S    973
           Δ
2941  ctcctctgcttatactggaaggccaggaagttgtcaacactgcgttccaacacacggaaa  3000
 974   L   L   C   L   Y   W   K   A   R   K   L   S   T   L   R   S   N   T   R   K    993
              Δ
3001  gaaaagctctctgggtggacttgaaagaggctggaggtgtgaccacaaataggagggaa  3060
 994   E   K   A   L   W   V   D   L   K   E   A   G   G   V   T   T   N   R   R   E    1013

3061  gacgaggaggaagatgaaggcaactgaatcccaagaggcacctgcagccaggaaggaaag  3120
1014   D   E   E   E   D   E   G   N   *                                                1021

3121  ccccgtgtggaatgtggtgacctagtcacctggaaccagctcctgacagaccccggcaac  3180

3181  ttctagatgaacccaagtgaactttcctcattaccatcctgaagtcactaccccaggggg  3240

3241  agctatagcttcatgaccgtaacatgtgacctgtgtgctggcaggacgactcactgcggc  3300

3301  tgcgccactgggaccccTccCctacatgcaccaatgcacg                      3340
```

FIG. 7A-3

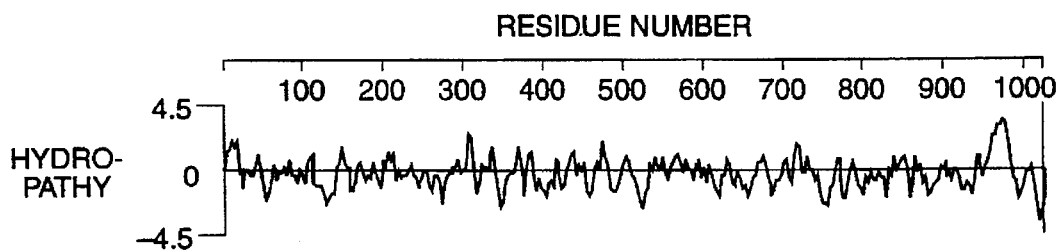

FIG. 7B

```
                    L         C                    W
IgSF-V   1
   VII    RVSKVYWTEN VTEHREVAIR CSLESVGSSA TLYS-VMWYW NRENSGSKLL
   VI     KVNSRSQGQE LSINSNTDIE CSILSRSNGN LQL-AIIWYF SPVSTNASWL
   V      QVSLMSRQPQ VMLTNTFDLS CVVRAGYSDL KVPLTVTWQF QPASSHIFHQ
   IV     VVSTKNKQQV VWEGETLAFL CKAGGAESPL ---SVSWWH IPRDQTQPEF
   III    FQVNITADSL FAEGKPLELV CLVVSSGRDP QLQG--IWFF NGTEIAHIDA
   II     SATMSSQTLG KEEGEPLALT CEASKATAQH THL-SVTWYL TQDGGGSQAT
   I      DVTVQKGPLFR AEGYPVSIG CNVTGHQGPS EQH--FQWSV YLPTNPTQEV
Consensus .Vs..s..q. v.EG.plal. C.v.s..s.. ........ .V.Wyf .p.ss.s...l R             F  L   I                    100
IgSF-V   51
   VII    VHLQH-DGLL EYGEE----G LRRHLHCYRS S--STD-FVL KLHQV-E-ME
   VI     KILEMDQTNV IKTGDEFHTP QRKQKFHT-- EKVSQDLFQL HILNV-E-DS
   V      LIRITHNGTI EWGN----FL SRFQKKT--- -KVSQSLFRS QLLVHDATEE
   IV     VAGMGQDGIV QLGASYGVPS YHGNTRL--- EKMDWATFQL EITFT-A-IT
   III    GGVLGLKN-- DY-K------ ERASQGELQL SKLGPKAFSL KI-FS-LGPE
   II     EIISLSKDFI LVPGPLY--T ERFAASDVQL NKLGPTTFRL SI-ERLQS-S
   I      QIIS-TKDAA -FSYAVY--T QRVRGGDVYV ERVQGNSVLL HI-SKLQM-K
Consensus vI....kg.. eyg....... qR.q..dv.. eKvs.d.F.L .I........

131
IgSF-V   101  D  G  Y  C
   VII    DAGMYWCRVA EWQLHGHPSK -W--I-NQAS D
   VI     DRGKYHCAVE EWLLSTNGT- -WHKLGEKK- -
   V      ETGVYQCEV- EVYD-RN-S- LYNNRPPRAS A
   IV     DSGTYECRVS E--KSRNQAR DLS-WTQKIS -
   III    DEGAYRCVVA EVMKTRTGS- -WQ-VLQRKQ -
   II     DQGQLFCEAT EWIQDPDET- -WM-FITKKQ -
   I      DAGEYECHTP NTDENYYGS- -Y-RAKTNLI -
Consensus D.G.Y.C.V. Ew..srngS. .W....qkks .
```

FIG. 8

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: unknown (  i i  ) MOLECULE TYPE: peptide (  i x  ) FEATURE:
  ( A ) NAME/KEY: Peptide
  ( B ) LOCATION: 1..7
  ( D ) OTHER INFORMATION: /note="Conserved motif at the
    COOH- terminal end of the putative ARAg Ig domains."

(  x i  ) SEQUENCE DESCRIPTION: SEQ ID NO:1:

Asp Xaa Gly Xaa Tyr Xaa Cys
1         5

( 2 ) INFORMATION FOR SEQ ID NO:2:

( i ) SEQUENCE CHARACTERISTICS:
  ( A ) LENGTH: 3340 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: CDS
  ( B ) LOCATION: 22..3084

( x i ) SEQUENCE DESCRIPTION: SEQ ID NO:2:

```
CTCTAAAGCT TTAGAGCCCA A ATG GCA GGC ATC TCA TAT GTG GCA TCT TTC         51
                        Met Ala Gly Ile Ser Tyr Val Ala Ser Phe
                         1           5                        10

TTT CTC CTT CTG ACT AAG CTC AGC ATT GGC CAG AGA GAA GTA ACA GTT         99
Phe Leu Leu Leu Thr Lys Leu Ser Ile Gly Gln Arg Glu Val Thr Val
             15                  20                  25

CAG AAA GGA CCA CTG TTT AGA GCT GAA GGT TAC CCA GTC AGC ATT GGC        147
Gln Lys Gly Pro Leu Phe Arg Ala Glu Gly Tyr Pro Val Ser Ile Gly
                 30                  35                  40

TGC AAT GTA ACT GGC CAC CAG GGA CCT TCT GAG CAG CAT TTC CAG TGG        195
Cys Asn Val Thr Gly His Gln Gly Pro Ser Glu Gln His Phe Gln Trp
             45                  50                  55

TCT GTT TAC CTG CCG ACA AAC CCG ACC CAG GAA GTC CAG ATC ATT AGC        243
Ser Val Tyr Leu Pro Thr Asn Pro Thr Gln Glu Val Gln Ile Ile Ser
         60                  65                  70

ACC AAG GAT GCT GCC TTC TCT TAC GCA GTA TAT ACG CAG CGG GTG CGA        291
Thr Lys Asp Ala Ala Phe Ser Tyr Ala Val Tyr Thr Gln Arg Val Arg
 75                  80                  85                  90

GGC GGA GAC GTC TAC GTG GAG AGG GTC CAG GGC AAC TCA GTC TTG TTG        339
Gly Gly Asp Val Tyr Val Glu Arg Val Gln Gly Asn Ser Val Leu Leu
                 95                 100                 105

CAC ATC TCA AAA CTC CAG ATG AAG GAT GCT GGC GAG TAT GAG TGT CAC        387
His Ile Ser Lys Leu Gln Met Lys Asp Ala Gly Glu Tyr Glu Cys His
             110                 115                 120

ACA CCA AAC ACT GAT GAG AAT TAC TAT GGA AGT TAC AGA GCA AAG ACT        435
Thr Pro Asn Thr Asp Glu Asn Tyr Tyr Gly Ser Tyr Arg Ala Lys Thr
         125                 130                 135

AAT CTA ATT GTT ATT CCA GAT ACC CTC TCT GCC ACC ATG AGT TCT CAG        483
Asn Leu Ile Val Ile Pro Asp Thr Leu Ser Ala Thr Met Ser Ser Gln
     140                 145                 150

ACT CTC GGT AAG GAG GAA GGT GAG CCA TTA GCC CTC ACC TGT GAG GCA        531
Thr Leu Gly Lys Glu Glu Gly Glu Pro Leu Ala Leu Thr Cys Glu Ala
155                 160                 165                 170

TCC AAA GCC ACA GCC CAA CAT ACT CAC CTC TCT GTC ACC TGG TAC CTA        579
Ser Lys Ala Thr Ala Gln His Thr His Leu Ser Val Thr Trp Tyr Leu
             175                 180                 185

ACA CAG GAT GGA GGA GGA AGC CAA GCC ACT GAG ATT ATT TCT CTC TCC        627
Thr Gln Asp Gly Gly Gly Ser Gln Ala Thr Glu Ile Ile Ser Leu Ser
```

|     |     |     |     |     | 190 |     |     |     |     | 195 |     |     |     |     | 200 |     |      |
|-----|-----|-----|-----|-----|-----|-----|-----|-----|-----|-----|-----|-----|-----|-----|-----|-----|------|
| AAA | GAT | TTT | ATA | TTG | GTC | CCT | GGG | CCC | TTG | TAT | ACA | GAG | CGG | TTT | GCA |     | 675  |
| Lys | Asp | Phe | Ile | Leu | Val | Pro | Gly | Pro | Leu | Tyr | Thr | Glu | Arg | Phe | Ala |     |      |
|     |     | 205 |     |     |     |     | 210 |     |     |     |     | 215 |     |     |     |     |      |
| GCC | AGT | GAC | GTA | CAG | CTC | AAC | AAA | CTG | GGA | CCC | ACT | ACA | TTC | AGG | CTG |     | 723  |
| Ala | Ser | Asp | Val | Gln | Leu | Asn | Lys | Leu | Gly | Pro | Thr | Thr | Phe | Arg | Leu |     |      |
|     | 220 |     |     |     |     | 225 |     |     |     |     | 230 |     |     |     |     |     |      |
| TCC | ATA | GAG | AGG | CTC | CAG | TCC | TCA | GAT | CAG | GGT | CAG | CTG | TTC | TGT | GAG |     | 771  |
| Ser | Ile | Glu | Arg | Leu | Gln | Ser | Ser | Asp | Gln | Gly | Gln | Leu | Phe | Cys | Glu |     |      |
| 235 |     |     |     |     | 240 |     |     |     |     | 245 |     |     |     |     | 250 |     |      |
| GCA | ACG | GAA | TGG | ATT | CAG | GAT | CCA | GAT | GAA | ACT | TGG | ATG | TTC | ATC | ACC |     | 819  |
| Ala | Thr | Glu | Trp | Ile | Gln | Asp | Pro | Asp | Glu | Thr | Trp | Met | Phe | Ile | Thr |     |      |
|     |     |     |     | 255 |     |     |     |     | 260 |     |     |     |     | 265 |     |     |      |
| AAA | AAG | CAG | ACC | GAT | CAA | ACC | ACT | CTG | AGG | ATC | CAG | CCA | GCA | GTG | AAA |     | 867  |
| Lys | Lys | Gln | Thr | Asp | Gln | Thr | Thr | Leu | Arg | Ile | Gln | Pro | Ala | Val | Lys |     |      |
|     |     |     | 270 |     |     |     |     | 275 |     |     |     |     | 280 |     |     |     |      |
| GAT | TTT | CAA | GTC | AAC | ATT | ACA | GCT | GAC | AGC | TTG | TTT | GCT | GAA | GGG | AAA |     | 915  |
| Asp | Phe | Gln | Val | Asn | Ile | Thr | Ala | Asp | Ser | Leu | Phe | Ala | Glu | Gly | Lys |     |      |
|     |     | 285 |     |     |     |     | 290 |     |     |     |     | 295 |     |     |     |     |      |
| CCC | TTA | GAA | CTG | GTT | TGC | CTG | GTT | GTA | AGC | AGT | GGC | CGT | GAC | CCA | CAG |     | 963  |
| Pro | Leu | Glu | Leu | Val | Cys | Leu | Val | Val | Ser | Ser | Gly | Arg | Asp | Pro | Gln |     |      |
|     | 300 |     |     |     |     | 305 |     |     |     |     | 310 |     |     |     |     |     |      |
| CTT | CAA | GGC | ATT | TGG | TTC | TTC | AAT | GGG | ACT | GAA | ATT | GCT | CAC | ATT | GAT |     | 1011 |
| Leu | Gln | Gly | Ile | Trp | Phe | Phe | Asn | Gly | Thr | Glu | Ile | Ala | His | Ile | Asp |     |      |
| 315 |     |     |     |     | 320 |     |     |     |     | 325 |     |     |     |     | 330 |     |      |
| GCT | GGT | GGA | GTC | CTG | GGC | CTG | AAG | AAT | GAC | TAC | AAA | GAG | AGA | GCA | AGT |     | 1059 |
| Ala | Gly | Gly | Val | Leu | Gly | Leu | Lys | Asn | Asp | Tyr | Lys | Glu | Arg | Ala | Ser |     |      |
|     |     |     |     | 335 |     |     |     |     | 340 |     |     |     |     | 345 |     |     |      |
| CAA | GGA | GAG | CTC | CAG | CTT | TCA | AAG | TTA | GGC | CCC | AAG | GCT | TTC | TCT | CTC |     | 1107 |
| Gln | Gly | Glu | Leu | Gln | Leu | Ser | Lys | Leu | Gly | Pro | Lys | Ala | Phe | Ser | Leu |     |      |
|     |     |     | 350 |     |     |     |     | 355 |     |     |     |     | 360 |     |     |     |      |
| AAG | ATC | TTC | TCT | CTG | GGC | CCA | GAG | GAT | GAA | GGC | GCC | TAC | AGA | TGT | GTG |     | 1155 |
| Lys | Ile | Phe | Ser | Leu | Gly | Pro | Glu | Asp | Glu | Gly | Ala | Tyr | Arg | Cys | Val |     |      |
|     |     | 365 |     |     |     |     | 370 |     |     |     |     | 375 |     |     |     |     |      |
| GTA | GCA | GAG | GTC | ATG | AAA | ACA | CGC | ACA | GGT | TCC | TGG | CAG | GTG | CTT | CAG |     | 1203 |
| Val | Ala | Glu | Val | Met | Lys | Thr | Arg | Thr | Gly | Ser | Trp | Gln | Val | Leu | Gln |     |      |
|     | 380 |     |     |     |     | 385 |     |     |     |     | 390 |     |     |     |     |     |      |
| AGA | AAG | CAG | TCA | CCA | GAC | AGC | CAC | GTG | CAC | CTG | AGG | AAG | CCA | GCA | GCA |     | 1251 |
| Arg | Lys | Gln | Ser | Pro | Asp | Ser | His | Val | His | Leu | Arg | Lys | Pro | Ala | Ala |     |      |
| 395 |     |     |     | 400 |     |     |     |     | 405 |     |     |     |     | 410 |     |     |      |
| AGA | AGT | GTG | GTC | GTG | TCT | ACC | AAG | AAC | AAG | CAG | CAA | GTT | GTG | TGG | GAA |     | 1299 |
| Arg | Ser | Val | Val | Val | Ser | Thr | Lys | Asn | Lys | Gln | Gln | Val | Val | Trp | Glu |     |      |
|     |     |     |     | 415 |     |     |     |     | 420 |     |     |     |     | 425 |     |     |      |
| GGA | GAG | ACA | CTC | GCC | TTT | CTC | TGT | AAG | GCT | GGT | GGA | GCT | GAA | AGT | CCC |     | 1347 |
| Gly | Glu | Thr | Leu | Ala | Phe | Leu | Cys | Lys | Ala | Gly | Gly | Ala | Glu | Ser | Pro |     |      |
|     |     |     | 430 |     |     |     |     | 435 |     |     |     |     | 440 |     |     |     |      |
| CTG | TCT | GTG | AGC | TGG | TGG | CAC | ATC | CCA | CGG | GAC | CAG | ACA | CAG | CCC | GAG |     | 1395 |
| Leu | Ser | Val | Ser | Trp | Trp | His | Ile | Pro | Arg | Asp | Gln | Thr | Gln | Pro | Glu |     |      |
|     |     |     | 445 |     |     |     |     | 450 |     |     |     |     | 455 |     |     |     |      |
| TTT | GTG | GCT | GGC | ATG | GGG | CAG | GAT | GGC | ATT | GTG | CAG | CTG | GGT | GCC | TCC |     | 1443 |
| Phe | Val | Ala | Gly | Met | Gly | Gln | Asp | Gly | Ile | Val | Gln | Leu | Gly | Ala | Ser |     |      |
|     |     | 460 |     |     |     |     | 465 |     |     |     |     | 470 |     |     |     |     |      |
| TAT | GGG | GTA | CCC | AGT | TAC | CAT | GGC | AAC | ACA | AGG | CTG | GAG | AAA | ATG | GAC |     | 1491 |
| Tyr | Gly | Val | Pro | Ser | Tyr | His | Gly | Asn | Thr | Arg | Leu | Glu | Lys | Met | Asp |     |      |
| 475 |     |     |     |     | 480 |     |     |     |     | 485 |     |     |     |     | 490 |     |      |
| TGG | GCC | ACC | TTC | CAG | CTG | GAG | ATC | ACC | TTC | ACT | GCC | ATC | ACA | GAC | AGT |     | 1539 |
| Trp | Ala | Thr | Phe | Gln | Leu | Glu | Ile | Thr | Phe | Thr | Ala | Ile | Thr | Asp | Ser |     |      |
|     |     |     |     | 495 |     |     |     |     | 500 |     |     |     |     | 505 |     |     |      |
| GGC | ACA | TAT | GAG | TGC | AGA | GTA | TCT | GAG | AAG | TCT | CGG | AAC | CAG | GCC | AGA |     | 1587 |
| Gly | Thr | Tyr | Glu | Cys | Arg | Val | Ser | Glu | Lys | Ser | Arg | Asn | Gln | Ala | Arg |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 510 |     |     |     |     | 515 |     |     |     |     | 520 |     |      |
| GAT | CTG | AGC | TGG | ACT | CAG | AAG | ATT | TCA | GTT | ACT | GTA | AAG | TCT | CTG | GAG | 1635 |
| Asp | Leu | Ser | Trp | Thr | Gln | Lys | Ile | Ser | Val | Thr | Val | Lys | Ser | Leu | Glu |      |
|     |     | 525 |     |     |     |     | 530 |     |     |     |     | 535 |     |     |     |      |
| TCA | AGT | TTA | CAA | GTT | AGT | CTG | ATG | AGC | CGT | CAG | CCG | CAG | GTG | ATG | TTA | 1683 |
| Ser | Ser | Leu | Gln | Val | Ser | Leu | Met | Ser | Arg | Gln | Pro | Gln | Val | Met | Leu |      |
|     | 540 |     |     |     |     | 545 |     |     |     |     | 550 |     |     |     |     |      |
| ACC | AAC | ACC | TTT | GAC | CTG | TCC | TGT | GTC | GTG | AGG | GCC | GGT | TAC | TCT | GAC | 1731 |
| Thr | Asn | Thr | Phe | Asp | Leu | Ser | Cys | Val | Val | Arg | Ala | Gly | Tyr | Ser | Asp |      |
| 555 |     |     |     |     | 560 |     |     |     |     | 565 |     |     |     |     | 570 |      |
| CTC | AAG | GTG | CCA | CTC | ACT | GTG | ACG | TGG | CAG | TTC | CAG | CCA | GCT | AGC | TCT | 1779 |
| Leu | Lys | Val | Pro | Leu | Thr | Val | Thr | Trp | Gln | Phe | Gln | Pro | Ala | Ser | Ser |      |
|     |     |     |     | 575 |     |     |     |     | 580 |     |     |     |     | 585 |     |      |
| CAC | ATA | TTC | CAC | CAG | CTT | ATT | CGA | ATC | ACC | CAC | AAT | GGC | ACT | ATT | GAA | 1827 |
| His | Ile | Phe | His | Gln | Leu | Ile | Arg | Ile | Thr | His | Asn | Gly | Thr | Ile | Glu |      |
|     |     |     | 590 |     |     |     |     | 595 |     |     |     |     | 600 |     |     |      |
| TGG | GGG | AAT | TTC | CTA | TCC | CGG | TTC | CAA | AAG | AAG | ACG | AAA | GTG | TCG | CAG | 1875 |
| Trp | Gly | Asn | Phe | Leu | Ser | Arg | Phe | Gln | Lys | Lys | Thr | Lys | Val | Ser | Gln |      |
|     |     | 605 |     |     |     |     | 610 |     |     |     |     | 615 |     |     |     |      |
| TCT | TTA | TTT | CGT | TCA | CAA | CTC | CTA | GTC | CAT | GAT | GCC | ACT | GAG | GAA | GAG | 1923 |
| Ser | Leu | Phe | Arg | Ser | Gln | Leu | Leu | Val | His | Asp | Ala | Thr | Glu | Glu | Glu |      |
|     | 620 |     |     |     |     | 625 |     |     |     |     | 630 |     |     |     |     |      |
| ACA | GGA | GTG | TAT | CAG | TGT | GAA | GTA | GAA | GTT | TAT | GAC | AGA | AAT | TCC | CTA | 1971 |
| Thr | Gly | Val | Tyr | Gln | Cys | Glu | Val | Glu | Val | Tyr | Asp | Arg | Asn | Ser | Leu |      |
| 635 |     |     |     |     | 640 |     |     |     |     | 645 |     |     |     |     | 650 |      |
| TAC | AAC | AAC | CGC | CCC | CCG | AGG | GCT | TCT | GCC | ATC | TCT | CAC | CCA | CTG | AGG | 2019 |
| Tyr | Asn | Asn | Arg | Pro | Pro | Arg | Ala | Ser | Ala | Ile | Ser | His | Pro | Leu | Arg |      |
|     |     |     |     | 655 |     |     |     |     | 660 |     |     |     |     | 665 |     |      |
| ATA | GCC | GTC | ACT | TTA | CCA | GAG | AGC | AAG | CTA | AAA | GTG | AAT | TCA | AGG | AGT | 2067 |
| Ile | Ala | Val | Thr | Leu | Pro | Glu | Ser | Lys | Leu | Lys | Val | Asn | Ser | Arg | Ser |      |
|     |     |     | 670 |     |     |     |     | 675 |     |     |     |     | 680 |     |     |      |
| CAA | GGG | CAA | GAG | CTC | TCC | ATC | AAC | TCC | AAC | ACT | GAT | ATA | GAA | TGT | AGC | 2115 |
| Gln | Gly | Gln | Glu | Leu | Ser | Ile | Asn | Ser | Asn | Thr | Asp | Ile | Glu | Cys | Ser |      |
|     |     | 685 |     |     |     |     | 690 |     |     |     |     | 695 |     |     |     |      |
| ATC | TTG | TCC | CGG | TCC | AAT | GGA | AAC | CTT | CAG | TTA | GCC | ATT | ATT | TGG | TAT | 2163 |
| Ile | Leu | Ser | Arg | Ser | Asn | Gly | Asn | Leu | Gln | Leu | Ala | Ile | Ile | Trp | Tyr |      |
|     | 700 |     |     |     |     | 705 |     |     |     |     | 710 |     |     |     |     |      |
| TTT | TCT | CCT | GTT | TCC | ACT | AAT | GCC | TCT | TGG | CTA | AAG | ATC | CTG | GAG | ATG | 2211 |
| Phe | Ser | Pro | Val | Ser | Thr | Asn | Ala | Ser | Trp | Leu | Lys | Ile | Leu | Glu | Met |      |
| 715 |     |     |     |     | 720 |     |     |     |     | 725 |     |     |     |     | 730 |      |
| GAC | CAA | ACC | AAT | GTT | ATA | AAA | ACT | GGG | GAT | GAG | TTT | CAC | ACC | CCA | CAG | 2259 |
| Asp | Gln | Thr | Asn | Val | Ile | Lys | Thr | Gly | Asp | Glu | Phe | His | Thr | Pro | Gln |      |
|     |     |     |     | 735 |     |     |     |     | 740 |     |     |     |     | 745 |     |      |
| AGA | AAA | CAA | AAA | TTT | CAT | ACT | GAG | AAG | GTT | TCC | CAA | GAC | TTA | TTT | CAG | 2307 |
| Arg | Lys | Gln | Lys | Phe | His | Thr | Glu | Lys | Val | Ser | Gln | Asp | Leu | Phe | Gln |      |
|     |     |     | 750 |     |     |     |     | 755 |     |     |     |     | 760 |     |     |      |
| CTG | CAC | ATT | CTG | AAT | GTG | GAA | GAC | AGC | GAT | CGG | GGC | AAA | TAT | CAC | TGT | 2355 |
| Leu | His | Ile | Leu | Asn | Val | Glu | Asp | Ser | Asp | Arg | Gly | Lys | Tyr | His | Cys |      |
|     |     | 765 |     |     |     |     | 770 |     |     |     |     | 775 |     |     |     |      |
| GCT | GTG | GAG | GAA | TGG | CTC | CTG | TCT | ACA | AAT | GGC | ACT | TGG | CAC | AAG | CTT | 2403 |
| Ala | Val | Glu | Glu | Trp | Leu | Leu | Ser | Thr | Asn | Gly | Thr | Trp | His | Lys | Leu |      |
|     | 780 |     |     |     |     | 785 |     |     |     |     | 790 |     |     |     |     |      |
| GGA | GAA | AAG | AAG | TCA | GGA | CTA | ACA | GAA | TTG | AAA | CTC | AAG | CCC | ACA | GGA | 2451 |
| Gly | Glu | Lys | Lys | Ser | Gly | Leu | Thr | Glu | Leu | Lys | Leu | Lys | Pro | Thr | Gly |      |
| 795 |     |     |     |     | 800 |     |     |     |     | 805 |     |     |     |     | 810 |      |
| AGT | AAG | GTA | CGT | GTC | TCC | AAA | GTG | TAC | TGG | ACC | GAA | AAT | GTG | ACT | GAG | 2499 |
| Ser | Lys | Val | Arg | Val | Ser | Lys | Val | Tyr | Trp | Thr | Glu | Asn | Val | Thr | Glu |      |
|     |     |     |     | 815 |     |     |     |     | 820 |     |     |     |     | 825 |     |      |
| CAC | AGA | GAA | GTG | GCC | ATC | CGC | TGC | AGC | CTG | GAG | AGT | GTA | GGC | AGC | TCA | 2547 |
| His | Arg | Glu | Val | Ala | Ile | Arg | Cys | Ser | Leu | Glu | Ser | Val | Gly | Ser | Ser |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| GCC | ACT | CTG | TAC | TCT | GTG | ATG | TGG | TAC | TGG | AAC | AGA | GAA | AAC | TCT | GGA | 2595 |
| Ala | Thr | Leu | Tyr | Ser | Val | Met | Trp | Tyr | Trp | Asn | Arg | Glu | Asn | Ser | Gly |      |
|     |     | 845 |     |     |     |     | 850 |     |     |     |     | 855 |     |     |     |      |
| AGT | AAA | TTG | CTG | GTG | CAC | TTG | CAA | CAT | GAT | GGC | TTG | CTG | GAG | TAT | GGG | 2643 |
| Ser | Lys | Leu | Leu | Val | His | Leu | Gln | His | Asp | Gly | Leu | Leu | Glu | Tyr | Gly |      |
|     | 860 |     |     |     |     | 865 |     |     |     |     | 870 |     |     |     |     |      |
| GAA | GAG | GGG | CTC | AGG | AGG | CAC | CTG | CAC | TGT | TAC | CGT | TCA | TCC | TCT | ACA | 2691 |
| Glu | Glu | Gly | Leu | Arg | Arg | His | Leu | His | Cys | Tyr | Arg | Ser | Ser | Ser | Thr |      |
| 875 |     |     |     |     | 880 |     |     |     |     | 885 |     |     |     |     | 890 |      |
| GAC | TTT | GTC | CTG | AAG | CTT | CAT | CAG | GTG | GAG | ATG | GAG | GAT | GCA | GGA | ATG | 2739 |
| Asp | Phe | Val | Leu | Lys | Leu | His | Gln | Val | Glu | Met | Glu | Asp | Ala | Gly | Met |      |
|     |     |     |     | 895 |     |     |     |     | 900 |     |     |     |     | 905 |     |      |
| TAC | TGG | TGT | AGG | GTG | GCA | GAG | TGG | CAG | CTC | CAT | GGA | CAC | CCA | AGC | AAG | 2787 |
| Tyr | Trp | Cys | Arg | Val | Ala | Glu | Trp | Gln | Leu | His | Gly | His | Pro | Ser | Lys |      |
|     |     |     | 910 |     |     |     |     | 915 |     |     |     |     | 920 |     |     |      |
| TGG | ATT | AAT | CAA | GCA | TCC | GAT | GAG | TCA | CAG | CGG | ATG | GTG | CTC | ACG | GTG | 2835 |
| Trp | Ile | Asn | Gln | Ala | Ser | Asp | Glu | Ser | Gln | Arg | Met | Val | Leu | Thr | Val |      |
|     |     | 925 |     |     |     |     | 930 |     |     |     |     | 935 |     |     |     |      |
| CTG | CCT | TCA | GAG | CCC | ACG | CTT | CCT | TCC | AGG | ATC | TGC | TCC | TCG | GCC | CCT | 2883 |
| Leu | Pro | Ser | Glu | Pro | Thr | Leu | Pro | Ser | Arg | Ile | Cys | Ser | Ser | Ala | Pro |      |
|     | 940 |     |     |     |     | 945 |     |     |     |     | 950 |     |     |     |     |      |
| TTA | CTC | TAT | TTC | CTG | TTC | ATC | TGT | CCC | TTC | GTC | CTG | CTC | CTC | CTT | CTG | 2931 |
| Leu | Leu | Tyr | Phe | Leu | Phe | Ile | Cys | Pro | Phe | Val | Leu | Leu | Leu | Leu | Leu |      |
| 955 |     |     |     |     | 960 |     |     |     |     | 965 |     |     |     |     | 970 |      |
| CTC | ATC | TCC | CTC | CTC | TGC | TTA | TAC | TGG | AAG | GCC | AGG | AAG | TTG | TCA | ACA | 2979 |
| Leu | Ile | Ser | Leu | Leu | Cys | Leu | Tyr | Trp | Lys | Ala | Arg | Lys | Leu | Ser | Thr |      |
|     |     |     |     | 975 |     |     |     |     | 980 |     |     |     |     | 985 |     |      |
| CTG | CGT | TCC | AAC | ACA | CGG | AAA | GAA | AAA | GCT | CTC | TGG | GTG | GAC | TTG | AAA | 3027 |
| Leu | Arg | Ser | Asn | Thr | Arg | Lys | Glu | Lys | Ala | Leu | Trp | Val | Asp | Leu | Lys |      |
|     |     |     | 990 |     |     |     |     | 995 |     |     |     |     | 1000|     |     |      |
| GAG | GCT | GGA | GGT | GTG | ACC | ACA | AAT | AGG | AGG | GAA | GAC | GAG | GAG | GAA | GAT | 3075 |
| Glu | Ala | Gly | Gly | Val | Thr | Thr | Asn | Arg | Arg | Glu | Asp | Glu | Glu | Glu | Asp |      |
|     |     |     |     | 1005|     |     |     | 1010|     |     |     |     | 1015|     |     |      |
| GAA | GGC | AAC | TGAATCCCAA | GAGGCACCTG | CAGCCAGGAA | GGAAAGCCCC |  |  |  |  |  |  |  |  |  | 3124 |
| Glu | Gly | Asn |            |            |            |            |  |  |  |  |  |  |  |  |  |      |
|     |     | 1020|            |            |            |            |  |  |  |  |  |  |  |  |  |      |

```
GTGTGGAATG TGGTGACCTA GTCACCTGGA ACCAGCTCCT GACAGACCCC GGCAACTTCT        3184

AGATGAACCC AAGTGAACTT TCCTCATTAC CATCCTGAAG TCACTACCCC AGGGGGAGCT        3244

ATAGCTTCAT GACCGTAACA TGTGACCTGT GTGCTGGCAG GACGACTCAC TGCGGCTGCG        3304

CCACTGGGAC CCCTCCCCTA CATGCACCAA TGCACG                                  3340
```

( 2 ) INFORMATION FOR SEQ ID NO:3:

( i ) SEQUENCE CHARACTERISTICS:
       ( A ) LENGTH: 1021 amino acids
       ( B ) TYPE: amino acid
       ( D ) TOPOLOGY: linear ( i i ) MOLECULE TYPE: protein ( x i ) SEQUENCE DESCRIPTION: SEQ ID NO:3:

|     |     |     |     |     |     |     |     |     |     |     |     |     |     |     |
|-----|-----|-----|-----|-----|-----|-----|-----|-----|-----|-----|-----|-----|-----|-----|
| Met | Ala | Gly | Ile | Ser | Tyr | Val | Ala | Ser | Phe | Phe | Leu | Leu | Leu | Thr | Lys |
| 1   |     |     |     | 5   |     |     |     |     | 10  |     |     |     |     | 15  |
| Leu | Ser | Ile | Gly | Gln | Arg | Glu | Val | Thr | Val | Gln | Lys | Gly | Pro | Leu | Phe |
|     |     |     | 20  |     |     |     |     | 25  |     |     |     |     | 30  |     |
| Arg | Ala | Glu | Gly | Tyr | Pro | Val | Ser | Ile | Gly | Cys | Asn | Val | Thr | Gly | His |
|     |     | 35  |     |     |     |     | 40  |     |     |     |     | 45  |     |     |
| Gln | Gly | Pro | Ser | Glu | Gln | His | Phe | Gln | Trp | Ser | Val | Tyr | Leu | Pro | Thr |

-continued

| | 50 | | | | 55 | | | | 60 | | | | |
|---|---|---|---|---|---|---|---|---|---|---|---|---|---|
| Asn | Pro | Thr | Gln | Glu | Val | Gln | Ile | Ile | Ser | Thr | Lys | Asp | Ala | Ala | Phe |
| 65 | | | | | 70 | | | | 75 | | | | | | 80 |

Ser Tyr Ala Val Tyr Thr Gln Arg Val Arg Gly Gly Asp Val Tyr Val
                    85                  90                       95

Glu Arg Val Gln Gly Asn Ser Val Leu Leu His Ile Ser Lys Leu Gln
             100                 105                 110

Met Lys Asp Ala Gly Glu Tyr Glu Cys His Thr Pro Asn Thr Asp Glu
             115                 120                 125

Asn Tyr Tyr Gly Ser Tyr Arg Ala Lys Thr Asn Leu Ile Val Ile Pro
130                      135                 140

Asp Thr Leu Ser Ala Thr Met Ser Ser Gln Thr Leu Gly Lys Glu Glu
145                 150                 155                      160

Gly Glu Pro Leu Ala Leu Thr Cys Glu Ala Ser Lys Ala Thr Ala Gln
                 165                 170                 175

His Thr His Leu Ser Val Thr Trp Tyr Leu Thr Gln Asp Gly Gly Gly
             180                 185                 190

Ser Gln Ala Thr Glu Ile Ile Ser Leu Ser Lys Asp Phe Ile Leu Val
             195                 200                 205

Pro Gly Pro Leu Tyr Thr Glu Arg Phe Ala Ala Ser Asp Val Gln Leu
210                 215                 220

Asn Lys Leu Gly Pro Thr Thr Phe Arg Leu Ser Ile Glu Arg Leu Gln
225                      230                 235                 240

Ser Ser Asp Gln Gly Gln Leu Phe Cys Glu Ala Thr Glu Trp Ile Gln
                 245                 250                 255

Asp Pro Asp Glu Thr Trp Met Phe Ile Thr Lys Lys Gln Thr Asp Gln
             260                 265                 270

Thr Thr Leu Arg Ile Gln Pro Ala Val Lys Asp Phe Gln Val Asn Ile
         275                 280                 285

Thr Ala Asp Ser Leu Phe Ala Glu Gly Lys Pro Leu Glu Leu Val Cys
290                 295                 300

Leu Val Val Ser Ser Gly Arg Asp Pro Gln Leu Gln Gly Ile Trp Phe
305                 310                 315                      320

Phe Asn Gly Thr Glu Ile Ala His Ile Asp Ala Gly Gly Val Leu Gly
             325                 330                 335

Leu Lys Asn Asp Tyr Lys Glu Arg Ala Ser Gln Gly Glu Leu Gln Leu
             340                 345                 350

Ser Lys Leu Gly Pro Lys Ala Phe Ser Leu Lys Ile Phe Ser Leu Gly
             355                 360                 365

Pro Glu Asp Glu Gly Ala Tyr Arg Cys Val Val Ala Glu Val Met Lys
370                 375                 380

Thr Arg Thr Gly Ser Trp Gln Val Leu Gln Arg Lys Gln Ser Pro Asp
385                 390                 395                      400

Ser His Val His Leu Arg Lys Pro Ala Ala Arg Ser Val Val Val Ser
             405                 410                 415

Thr Lys Asn Lys Gln Gln Val Val Trp Glu Gly Glu Thr Leu Ala Phe
             420                 425                 430

Leu Cys Lys Ala Gly Gly Ala Glu Ser Pro Leu Ser Val Ser Trp Trp
             435                 440                 445

His Ile Pro Arg Asp Gln Thr Gln Pro Glu Phe Val Ala Gly Met Gly
             450                 455                 460

Gln Asp Gly Ile Val Gln Leu Gly Ala Ser Tyr Gly Val Pro Ser Tyr
465                 470                 475                      480

| | | | | | | | | | | | | | | |
|---|---|---|---|---|---|---|---|---|---|---|---|---|---|---|
| His | Gly | Asn | Thr | Arg | Leu | Glu | Lys | Met | Asp | Trp | Ala | Thr | Phe | Gln | Leu |
| | | | | 485 | | | | 490 | | | | | 495 | |
| Glu | Ile | Thr | Phe | Thr | Ala | Ile | Thr | Asp | Ser | Gly | Thr | Tyr | Glu | Cys | Arg |
| | | | 500 | | | | | 505 | | | | | 510 | | |
| Val | Ser | Glu | Lys | Ser | Arg | Asn | Gln | Ala | Arg | Asp | Leu | Ser | Trp | Thr | Gln |
| | | | 515 | | | | 520 | | | | | 525 | | | |
| Lys | Ile | Ser | Val | Thr | Val | Lys | Ser | Leu | Glu | Ser | Ser | Leu | Gln | Val | Ser |
| | 530 | | | | | 535 | | | | | 540 | | | | |
| Leu | Met | Ser | Arg | Gln | Pro | Gln | Val | Met | Leu | Thr | Asn | Thr | Phe | Asp | Leu |
| 545 | | | | | 550 | | | | | 555 | | | | | 560 |
| Ser | Cys | Val | Val | Arg | Ala | Gly | Tyr | Ser | Asp | Leu | Lys | Val | Pro | Leu | Thr |
| | | | | 565 | | | | | 570 | | | | | 575 | |
| Val | Thr | Trp | Gln | Phe | Gln | Pro | Ala | Ser | Ser | His | Ile | Phe | His | Gln | Leu |
| | | | 580 | | | | | 585 | | | | | 590 | | |
| Ile | Arg | Ile | Thr | His | Asn | Gly | Thr | Ile | Glu | Trp | Gly | Asn | Phe | Leu | Ser |
| | | | 595 | | | | 600 | | | | | 605 | | | |
| Arg | Phe | Gln | Lys | Lys | Thr | Lys | Val | Ser | Gln | Ser | Leu | Phe | Arg | Ser | Gln |
| | | 610 | | | | | 615 | | | | | 620 | | | |
| Leu | Leu | Val | His | Asp | Ala | Thr | Glu | Glu | Thr | Gly | Val | Tyr | Gln | Cys |
| 625 | | | | | 630 | | | | | 635 | | | | | 640 |
| Glu | Val | Glu | Val | Tyr | Asp | Arg | Asn | Ser | Leu | Tyr | Asn | Asn | Arg | Pro | Pro |
| | | | | 645 | | | | | 650 | | | | | 655 | |
| Arg | Ala | Ser | Ala | Ile | Ser | His | Pro | Leu | Arg | Ile | Ala | Val | Thr | Leu | Pro |
| | | | | 660 | | | | | 665 | | | | | 670 | |
| Glu | Ser | Lys | Leu | Lys | Val | Asn | Ser | Arg | Ser | Gln | Gly | Gln | Glu | Leu | Ser |
| | | | 675 | | | | | 680 | | | | | 685 | | |
| Ile | Asn | Ser | Asn | Thr | Asp | Ile | Glu | Cys | Ser | Ile | Leu | Ser | Arg | Ser | Asn |
| | | | 690 | | | | | 695 | | | | | 700 | | |
| Gly | Asn | Leu | Gln | Leu | Ala | Ile | Ile | Trp | Tyr | Phe | Ser | Pro | Val | Ser | Thr |
| 705 | | | | | 710 | | | | | 715 | | | | | 720 |
| Asn | Ala | Ser | Trp | Leu | Lys | Ile | Leu | Glu | Met | Asp | Gln | Thr | Asn | Val | Ile |
| | | | | 725 | | | | | 730 | | | | | 735 | |
| Lys | Thr | Gly | Asp | Glu | Phe | His | Thr | Pro | Gln | Arg | Lys | Gln | Lys | Phe | His |
| | | | 740 | | | | | 745 | | | | | 750 | | |
| Thr | Glu | Lys | Val | Ser | Gln | Asp | Leu | Phe | Gln | Leu | His | Ile | Leu | Asn | Val |
| | | 755 | | | | | 760 | | | | | 765 | | | |
| Glu | Asp | Ser | Asp | Arg | Gly | Lys | Tyr | His | Cys | Ala | Val | Glu | Glu | Trp | Leu |
| | 770 | | | | | 775 | | | | | 780 | | | | |
| Leu | Ser | Thr | Asn | Gly | Thr | Trp | His | Lys | Leu | Gly | Glu | Lys | Lys | Ser | Gly |
| 785 | | | | | 790 | | | | | 795 | | | | | 800 |
| Leu | Thr | Glu | Leu | Lys | Leu | Lys | Pro | Thr | Gly | Ser | Lys | Val | Arg | Val | Ser |
| | | | | 805 | | | | | 810 | | | | | 815 | |
| Lys | Val | Tyr | Trp | Thr | Glu | Asn | Val | Thr | Glu | His | Arg | Glu | Val | Ala | Ile |
| | | | | 820 | | | | | 825 | | | | | 830 | |
| Arg | Cys | Ser | Leu | Glu | Ser | Val | Gly | Ser | Ser | Ala | Thr | Leu | Tyr | Ser | Val |
| | | | 835 | | | | | 840 | | | | | 845 | | |
| Met | Trp | Tyr | Trp | Asn | Arg | Glu | Asn | Ser | Gly | Ser | Lys | Leu | Leu | Val | His |
| | | | 850 | | | | | 855 | | | | | 860 | | |
| Leu | Gln | His | Asp | Gly | Leu | Leu | Glu | Tyr | Gly | Glu | Glu | Gly | Leu | Arg | Arg |
| 865 | | | | | 870 | | | | | 875 | | | | | 880 |
| His | Leu | His | Cys | Tyr | Arg | Ser | Ser | Ser | Thr | Asp | Phe | Val | Leu | Lys | Leu |
| | | | | 885 | | | | | 890 | | | | | 895 | |
| His | Gln | Val | Glu | Met | Glu | Asp | Ala | Gly | Met | Tyr | Trp | Cys | Arg | Val | Ala |
| | | | | 900 | | | | | 905 | | | | | 910 | |

```
Glu  Trp  Gln  Leu  His  Gly  His  Pro  Ser  Lys  Trp  Ile  Asn  Gln  Ala  Ser
          915                 920                     925

Asp  Glu  Ser  Gln  Arg  Met  Val  Leu  Thr  Val  Leu  Pro  Ser  Glu  Pro  Thr
     930                      935                     940

Leu  Pro  Ser  Arg  Ile  Cys  Ser  Ser  Ala  Pro  Leu  Leu  Tyr  Phe  Leu  Phe
945                      950                     955                          960

Ile  Cys  Pro  Phe  Val  Leu  Leu  Leu  Leu  Leu  Ile  Ser  Leu  Leu  Cys
                    965                     970                     975

Leu  Tyr  Trp  Lys  Ala  Arg  Lys  Leu  Ser  Thr  Leu  Arg  Ser  Asn  Thr  Arg
               980                      985                     990

Lys  Glu  Lys  Ala  Leu  Trp  Val  Asp  Leu  Lys  Glu  Ala  Gly  Gly  Val  Thr
          995                      1000                    1005

Thr  Asn  Arg  Arg  Glu  Asp  Glu  Glu  Glu  Asp  Glu  Gly  Asn
     1010                    1015                    1020
```

( 2 ) INFORMATION FOR SEQ ID NO:4:

( i ) SEQUENCE CHARACTERISTICS:
        ( A ) LENGTH: 116 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Peptide
        ( B ) LOCATION: 1..116
        ( D ) OTHER INFORMATION: /note="A variable-type
            immunoglobulin-type domain of ARAg-h-1."

( x i ) SEQUENCE DESCRIPTION: SEQ ID NO:4:

```
Arg  Val  Ser  Lys  Val  Tyr  Trp  Thr  Glu  Asn  Val  Thr  Glu  His  Arg  Glu
1                   5                        10                          15

Val  Ala  Ile  Arg  Cys  Ser  Leu  Glu  Ser  Val  Gly  Ser  Ser  Ala  Thr  Leu
               20                       25                      30

Tyr  Ser  Val  Met  Trp  Tyr  Trp  Asn  Arg  Glu  Asn  Ser  Gly  Ser  Lys  Leu
          35                       40                      45

Leu  Val  His  Leu  Gln  His  Asp  Gly  Leu  Leu  Glu  Tyr  Gly  Glu  Glu  Gly
     50                       55                      60

Leu  Arg  Arg  His  Leu  His  Cys  Tyr  Arg  Ser  Ser  Ser  Thr  Asp  Phe  Val
65                       70                      75                            80

Leu  Lys  Leu  His  Gln  Val  Glu  Met  Glu  Asp  Ala  Gly  Met  Tyr  Trp  Cys
                    85                       90                          95

Arg  Val  Ala  Glu  Trp  Gln  Leu  His  Gly  His  Pro  Ser  Lys  Trp  Ile  Asn
               100                      105                     110

Gln  Ala  Ser  Asp
          115
```

( 2 ) INFORMATION FOR SEQ ID NO:5:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Peptide
        ( B ) LOCATION: 1..122
        ( D ) OTHER INFORMATION: /note="A variable -type -continued immunoglobulin-type domain of ARAg-h-1"

(xi) SEQUENCE DESCRIPTION: SEQ ID NO:5:

| Lys | Val | Asn | Ser | Arg | Ser | Gln | Gly | Gln | Glu | Leu | Ser | Ile | Asn | Ser | Asn |
|---|---|---|---|---|---|---|---|---|---|---|---|---|---|---|---|
| 1 | | | | 5 | | | | | 10 | | | | | 15 | |
| Thr | Asp | Ile | Glu | Cys | Ser | Ile | Leu | Ser | Arg | Ser | Asn | Gly | Asn | Leu | Gln |
| | | | 20 | | | | | 25 | | | | | 30 | | |
| Leu | Ala | Ile | Ile | Trp | Tyr | Phe | Ser | Pro | Val | Ser | Thr | Asn | Ala | Ser | Trp |
| | | | 35 | | | | 40 | | | | | 45 | | | |
| Leu | Lys | Ile | Leu | Glu | Met | Asp | Gln | Thr | Asn | Val | Ile | Lys | Thr | Gly | Asp |
| | 50 | | | | | 55 | | | | | 60 | | | | |
| Glu | Phe | His | Thr | Pro | Gln | Arg | Lys | Gln | Lys | Phe | His | Thr | Glu | Lys | Val |
| 65 | | | | | 70 | | | | | 75 | | | | | 80 |
| Ser | Gln | Asp | Leu | Phe | Gln | Leu | His | Ile | Leu | Asn | Val | Glu | Asp | Ser | Asp |
| | | | | 85 | | | | | 90 | | | | | 95 | |
| Arg | Gly | Lys | Tyr | His | Cys | Ala | Val | Glu | Glu | Trp | Leu | Leu | Ser | Thr | Asn |
| | | | | 100 | | | | | 105 | | | | | 110 | |
| Gly | Thr | Trp | His | Lys | Leu | Gly | Glu | Lys | Lys | | | | | | |
| | | 115 | | | | | 120 | | | | | | | | |

(2) INFORMATION FOR SEQ ID NO:6:

(i) SEQUENCE CHARACTERISTICS:
  (A) LENGTH: 119 amino acids
  (B) TYPE: amino acid
  (C) STRANDEDNESS: single
  (D) TOPOLOGY: unknown (ii) MOLECULE TYPE: peptide (ix) FEATURE:
  (A) NAME/KEY: Peptide
  (B) LOCATION: 1..119
  (D) OTHER INFORMATION: /note="A variable-type immunoglobulin-type domain of ARAg-h-1."

(xi) SEQUENCE DESCRIPTION: SEQ ID NO:6:

| Gln | Val | Ser | Leu | Met | Ser | Arg | Gln | Pro | Gln | Val | Met | Leu | Thr | Asn | Thr |
|---|---|---|---|---|---|---|---|---|---|---|---|---|---|---|---|
| 1 | | | | 5 | | | | | 10 | | | | | 15 | |
| Phe | Asp | Leu | Ser | Cys | Val | Val | Arg | Ala | Gly | Tyr | Ser | Asp | Leu | Lys | Val |
| | | | 20 | | | | | 25 | | | | | 30 | | |
| Pro | Leu | Thr | Val | Thr | Trp | Gln | Phe | Gln | Pro | Ala | Ser | Ser | His | Ile | Phe |
| | | 35 | | | | | 40 | | | | | 45 | | | |
| His | Gln | Leu | Ile | Arg | Ile | Thr | His | Asn | Gly | Thr | Ile | Glu | Trp | Gly | Asn |
| | 50 | | | | | 55 | | | | | 60 | | | | |
| Phe | Leu | Ser | Arg | Phe | Gln | Lys | Lys | Thr | Lys | Val | Ser | Gln | Ser | Leu | Phe |
| 65 | | | | | 70 | | | | | 75 | | | | | 80 |
| Arg | Ser | Gln | Leu | Leu | Val | His | Asp | Ala | Thr | Glu | Glu | Glu | Thr | Gly | Val |
| | | | | 85 | | | | | 90 | | | | | 95 | |
| Tyr | Gln | Cys | Glu | Val | Glu | Val | Tyr | Asp | Arg | Asn | Ser | Leu | Tyr | Asn | Asn |
| | | | | 100 | | | | | 105 | | | | | 110 | |
| Arg | Pro | Pro | Arg | Ala | Ser | Ala | | | | | | | | | |
| | | | 115 | | | | | | | | | | | | |

(2) INFORMATION FOR SEQ ID NO:7:

(i) SEQUENCE CHARACTERISTICS:
  (A) LENGTH: 118 amino acids
  (B) TYPE: amino acid
  (C) STRANDEDNESS: single
  (D) TOPOLOGY: unknown (ii) MOLECULE TYPE: peptide (ix) FEATURE:
    (A) NAME/KEY: Peptide
    (B) LOCATION: 1..118
    (D) OTHER INFORMATION: /note="A variable-type immunoglobulin-type domain of ARAg-h-1."

(xi) SEQUENCE DESCRIPTION: SEQ ID NO:7:

```
Val Val Ser Thr Lys Asn Lys Gln Gln Val Val Trp Glu Gly Glu Thr
 1               5                  10                  15
Leu Ala Phe Leu Cys Lys Ala Gly Gly Ala Glu Ser Pro Leu Ser Val
                20                  25                  30
Ser Trp Trp His Ile Pro Arg Asp Gln Thr Gln Pro Glu Phe Val Ala
            35                  40                  45
Gly Met Gly Gln Asp Gly Ile Val Gln Leu Gly Ala Ser Tyr Gly Val
        50                  55                  60
Pro Ser Tyr His Gly Asn Thr Arg Leu Glu Lys Met Asp Trp Ala Thr
65                  70                  75                  80
Phe Gln Leu Glu Ile Thr Phe Thr Ala Ile Thr Asp Ser Gly Thr Tyr
                85                  90                  95
Glu Cys Arg Val Ser Glu Lys Ser Arg Asn Gln Ala Arg Asp Leu Ser
            100                 105                 110
Trp Thr Gln Lys Ile Ser
        115
```

(2) INFORMATION FOR SEQ ID NO:8:

(i) SEQUENCE CHARACTERISTICS:
        (A) LENGTH: 114 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Peptide
        (B) LOCATION: 1..114
        (D) OTHER INFORMATION: /note="A variable--type immunoglobulin-type domain of ARAg-h-1."

(xi) SEQUENCE DESCRIPTION: SEQ ID NO:8:

```
Phe Gln Val Asn Ile Thr Ala Asp Ser Leu Phe Ala Glu Gly Lys Pro
 1               5                  10                  15
Leu Glu Leu Val Cys Leu Val Val Ser Ser Gly Arg Asp Pro Gln Leu
                20                  25                  30
Gln Gly Ile Trp Phe Phe Asn Gly Thr Glu Ile Ala His Ile Asp Ala
            35                  40                  45
Gly Gly Val Leu Gly Leu Lys Asn Asp Tyr Lys Glu Arg Ala Ser Gln
        50                  55                  60
Gly Glu Leu Gln Leu Ser Lys Leu Gly Pro Lys Ala Phe Ser Leu Lys
65                  70                  75                  80
Ile Phe Ser Leu Gly Pro Glu Asp Glu Gly Ala Tyr Arg Cys Val Val
                85                  90                  95
Ala Glu Val Met Lys Thr Arg Thr Gly Ser Trp Gln Val Leu Gln Arg
            100                 105                 110
Lys Gln
```

(2) INFORMATION FOR SEQ ID NO:9:

(i) SEQUENCE CHARACTERISTICS:

( A ) LENGTH: 122 amino acids
( B ) TYPE: amino acid
( C ) STRANDEDNESS: single
( D ) TOPOLOGY: unknown ( i i ) MOLECULE TYPE: peptide ( i x ) FEATURE:
( A ) NAME/KEY: Peptide
( B ) LOCATION: 1..122
( D ) OTHER INFORMATION: /note="A variable-type
immunoglobulin-type domain of ARAg-h-1."

( x i ) SEQUENCE DESCRIPTION: SEQ ID NO:9:

| Ser | Ala | Thr | Met | Ser | Ser | Gln | Thr | Leu | Gly | Lys | Glu | Glu | Gly | Glu | Pro |
|---|---|---|---|---|---|---|---|---|---|---|---|---|---|---|---|
| 1 | | | | 5 | | | | | 10 | | | | | 15 | |
| Leu | Ala | Leu | Thr | Cys | Glu | Ala | Ser | Lys | Ala | Thr | Ala | Gln | His | Thr | His |
| | | | 20 | | | | 25 | | | | | 30 | | | |
| Leu | Ser | Val | Thr | Trp | Tyr | Leu | Thr | Gln | Asp | Gly | Gly | Gly | Ser | Gln | Ala |
| | | | 35 | | | | 40 | | | | | 45 | | | |
| Thr | Glu | Ile | Ile | Ser | Leu | Ser | Lys | Asp | Phe | Ile | Leu | Val | Pro | Gly | Pro |
| | | | 50 | | | | 55 | | | | | 60 | | | |
| Leu | Tyr | Thr | Glu | Arg | Phe | Ala | Ala | Ser | Asp | Val | Gln | Leu | Asn | Lys | Leu |
| 65 | | | | | 70 | | | | | 75 | | | | | 80 |
| Gly | Pro | Thr | Thr | Phe | Arg | Leu | Ser | Ile | Glu | Arg | Leu | Gln | Ser | Ser | Asp |
| | | | | 85 | | | | | 90 | | | | | 95 | |
| Gln | Gly | Gln | Leu | Phe | Cys | Glu | Ala | Thr | Glu | Trp | Ile | Gln | Asp | Pro | Asp |
| | | | 100 | | | | | 105 | | | | | 110 | | |
| Glu | Thr | Trp | Met | Phe | Ile | Thr | Lys | Lys | Gln | | | | | | |
| | | | 115 | | | | 120 | | | | | | | | |

( 2 ) INFORMATION FOR SEQ ID NO:10:

( i ) SEQUENCE CHARACTERISTICS:
( A ) LENGTH: 118 amino acids
( B ) TYPE: amino acid
( C ) STRANDEDNESS: single
( D ) TOPOLOGY: unknown ( i i ) MOLECULE TYPE: peptide ( i x ) FEATURE:
( A ) NAME/KEY: Peptide
( B ) LOCATION: 1..118
( D ) OTHER INFORMATION: /note="A variable-type
immunoglobulin-type domain of ARAg-h-1."

( x i ) SEQUENCE DESCRIPTION: SEQ ID NO:10:

| Val | Thr | Val | Gln | Lys | Gly | Pro | Leu | Phe | Arg | Ala | Glu | Gly | Tyr | Pro | Val |
|---|---|---|---|---|---|---|---|---|---|---|---|---|---|---|---|
| 1 | | | | 5 | | | | | 10 | | | | | 15 | |
| Ser | Ile | Gly | Cys | Asn | Val | Thr | Gly | His | Gln | Gly | Pro | Ser | Glu | Gln | His |
| | | | 20 | | | | 25 | | | | | 30 | | | |
| Phe | Gln | Trp | Ser | Val | Tyr | Leu | Pro | Thr | Asn | Pro | Thr | Gln | Glu | Val | Gln |
| | | | 35 | | | | 40 | | | | | 45 | | | |
| Ile | Ile | Ser | Thr | Lys | Asp | Ala | Ala | Phe | Ser | Tyr | Ala | Val | Tyr | Thr | Gln |
| | | | 50 | | | | 55 | | | | | 60 | | | |
| Arg | Val | Arg | Gly | Gly | Asp | Val | Tyr | Val | Glu | Arg | Val | Gln | Gly | Asn | Ser |
| 65 | | | | | 70 | | | | | 75 | | | | | 80 |
| Val | Leu | Leu | His | Ile | Ser | Lys | Leu | Gln | Met | Lys | Asp | Ala | Gly | Glu | Tyr |
| | | | | 85 | | | | | 90 | | | | | 95 | |
| Glu | Cys | His | Thr | Pro | Asn | Thr | Asp | Glu | Asn | Tyr | Tyr | Gly | Ser | Tyr | Arg |
| | | | 100 | | | | | 105 | | | | | 110 | | |
| Ala | Lys | Thr | Asn | Leu | Ile | | | | | | | | | | |

(2) INFORMATION FOR SEQ ID NO:11:

(i) SEQUENCE CHARACTERISTICS:
      (A) LENGTH: 130 amino acids
      (B) TYPE: amino acid
      (C) STRANDEDNESS: single
      (D) TOPOLOGY: unknown (ii) MOLECULE TYPE: peptide (ix) FEATURE:
      (A) NAME/KEY: Peptide
      (B) LOCATION: 1..130
      (D) OTHER INFORMATION: /note='"Xaa"can be any amino acid."

(xi) SEQUENCE DESCRIPTION: SEQ ID NO:11:

```
Xaa Val Ser Xaa Lys Ser Xaa Xaa Gln Xaa Val Xaa Glu Gly Xaa Xaa
 1               5                  10                  15
Leu Ala Leu Xaa Cys Xaa Val Xaa Ser Xaa Xaa Ser Xaa Xaa Xaa Xaa
            20                  25                  30
Xaa Xaa Xaa Val Xaa Trp Tyr Phe Xaa Pro Xaa Ser Ser Xaa Ser Xaa
        35                  40              45
Xaa Leu Val Ile Xaa Xaa Xaa Xaa Lys Gly Xaa Xaa Glu Tyr Gly Xaa
    50                      55              60
Xaa Xaa Xaa Xaa Xaa Thr Gln Arg Xaa Gln Xaa Xaa Asp Val Xaa Xaa
65                  70                  75                  80
Glu Lys Val Ser Xaa Asp Xaa Phe Xaa Leu Xaa Ile Xaa Xaa Xaa Xaa
                85                  90                  95
Xaa Xaa Xaa Xaa Asp Xaa Gly Xaa Tyr Xaa Cys Xaa Val Xaa Glu Trp
            100             105                 110
Xaa Xaa Ser Arg Asn Gly Ser Xaa Xaa Trp Xaa Xaa Xaa Xaa Gln Lys
        115             120                 125
Lys Xaa
    130
```

ALLOREACTION-ASSOCIATED ANTIGEN (ARAG): A NOVEL MEMBER OF THE IMMUNOGLOBULIN GENE SUPERFAMILY

CROSS REFERENCE TO RELATED APPLICATION

This application is a continuation-in-part of U.S. Ser. No. 08/149,212, filed Nov. 5, 1993, now abandoned, which is incorporated by reference in its entirety for all purposes.

STATEMENT OF GOVERNMENT INTEREST

This invention was made with Government support under contract CA24607 awarded by the National Institutes of Health. The Government has certain rights in this invention.

TECHNICAL FIELD

This invention relates generally to the identification of a novel cell-surface antigen, termed ARAg, and antibodies thereto, and the use of the antigen and antibodies for monitoring and/or modulating immune responses.

BACKGROUND OF THE INVENTION

Immune responses are largely mediated by a diverse collection of peripheral blood cells termed leukocytes. The leukocytes include lymphocytes, granulocytes and monocytes. Granulocytes are further subdivided into neutrophils, eosinophils and basophils. Lymphocytes are further subdivided into T and B lymphocytes. T-lymphocytes originate from lymphocytic-committed stem cells of the embryo. Differentiation occurs in the thymus and proceeds through prothymocyte, cortical thymocyte and medullary thymocyte intermediate stages, to produce various types of mature T-cells. These subtypes include CD8$^+$ T-cells (also known as cytotoxic/suppressor T-cells), which have the capacity to lyse target cells, and CD4$^+$ T-cells (also known as T helper and T inducer cells), which have the capacity to stimulate other immune system cell types.

Immune system responses are elicited in several differing situations. The most frequent response is as a desirable protection against infectious microorganisms. However, undesired immune response can occur following transplantation of foreign tissue, or in an autoimmune disease, in which one of a body's own antigens is the target for the immune response. Immune responses can also be initiated in vitro by mitogens or antibodies against certain receptors. In each of these situations, an immune response is transduced from a stimulating event via a complex interaction of leukocytic cell types. However, the participating cell types and nature of the interaction between cell types may vary for different stimulating events.

Much progress has recently been made in understanding the complex cellular interactions through which immune responses are mediated. Regulation occurs as the result of various cellular signals transduced between cells via soluble, as well as surface-bound, molecular mediators. Signals may be transduced either between a soluble mediator and a cell-surface antigen or between two cell surface antigens. Soluble mediators include interleukins, colony stimulating factors and the interferons, which interact with their respective receptors, for example, the IL-2 receptor. Paired cell surface antigens include LFA-1, and the ICAM's (Staunton et al., Cell 52:925 (1988); Staunton et al., Nature 339:61 (1989); Vazeux et al., Nature 360:485 (1992); CD2 and LFA-3 (Selvaraj et al., Nature 326:400 (1987), CD8 and HLA Class I (Norment et al., Nature 336:79 (1988), CD4 and HLA Class II (Doyle et al., Nature 330:256 (1987), CD28 and B7 (Linsley et al., Proc. Natl. Acad. Sci. USA 87:5031 (1990), as well as whole families of selectins, addressins and integrins (reviewed by Mackay et al., Immunology Today 14:99 (1993); Springer, Nature 346:425–434 (1990)) (each of which is incorporated by reference for all purposes).

Many of the cell-surface antigens and receptors identified to-date have been classified as members of the immunoglobulin superfamily of proteins (IgSF). IgSF proteins are characterized by one or more disulfide-linked loops formed between a highly conserved and properly spaced pair of cysteine residues, which organizes two β-sheets composed of seven or nine antiparallel β-strands. These loops, which are referred to as immunoglobulin-like domains, are subclassified as variable or constant immunoglobulin-type domains. The variable, or V-type domains, generally possess disulfide loops with cysteines spaced by 65–75 amino acids and thus accommodate nine antiparallel β-strands whereas the constant, or C-type, domains typically consist of intercysteine distances of 35–55 residues, and thus accommodate only seven antiparallel β-strands. Although some IgSF members contain multiple domains of a single type (e.g., NCAM with five C2-type domains), most members consist of either a single Ig domain or a mixture of domains of both the V- and C-types. In most members having a single Ig domain, the domain is variable (e.g., CTLA-4/CD28, Thy-1, $P_0$ (Williams et al., Ann. Rev. Immunol. 6:381 (1988); and newer members such as HB15 (Zhou et al., J. Immunol. 149:735 (1992), PD-1 (Ishida et al., EMBO J. 11:3887 (1992) and CMRF 35 (Jackson et al., European J. Immunol. 22:1157 (1992). In most members having multiple domains, the N-terminal domain (i.e., most externally orientated) is also usually of the variable type (e.g., all immunoglobulin and TCR chains, CD4, OX2, poly Ig receptor, carcinoembryonic antigen (reviewed in Williams et al., Ann. Rev. Immunol. 6:381 (1988) and newer members such as LAG-3 (Triebel et al., J. Exp. Med. 171:1393 (1990), Tactile (Wang et al., J. Immunol. 148:2600 (1992), CD33 (Simmons et al., J. Immunol. 141:2797 (1988) and BEN (Pourquie et al., Proc. Natl. Acad. Sci. USA 89:5261 (1992). The frequency with which V-type domains occur at the most externally oriented position suggests a particular importance of these domains in intercellular interactions.

The identification of signal-transducing cell-surface receptors has suggested new agents for suppressing undesirable immune responses such as transplant rejection, autoimmune disease and inflammation. Agents, particularly antibodies, that block receptors of immune cells from binding to soluble molecules or cell-bound receptors can impair immune responses. Ideally, an agent should block only undesired immune responses (e.g., transplant rejection) while leaving a residual capacity to effect desirable responses (e.g., responsive to pathogenic microorganisms). The immunosuppressive action of some agents, for example, antibodies against the CD3 receptor and the IL-2 receptor have already been tested in clinical trials. Although some trials have shown encouraging results, significant problems remain. First, a patient may develop an immune response toward the blocking agent preventing continued immunosuppressive effects unless different agents are available. Second, cells expressing the target antigen may be able to adapt to the presence of the blocking agent by ceasing to express the antigen, while retaining immune functions. In this situation, continued treatment with a single immunosuppressive agent is ineffective. Third, many agents, e.g., anti-CD3 antibodies, even though targeted against a specific receptor, effectively block all T-cell mediated immune responses, and thereby render a patient severely vulnerable to infection.

Based on the foregoing it is apparent that a need exists for additional and improved agents capable of suppressing immune responses, particularly agents capable of selective suppression. The present invention fulfills these and other needs, in part, by providing a novel cellular antigen as a novel target for immunosuppressive agents.

SUMMARY OF THE INVENTION

In one embodiment of the invention, purified ARAg polypeptides are provided. The amino acid and nucleotide sequences of one such ARAg polypeptide, termed ARAg-h-1, are shown in FIG. 7A. ARAg polypeptides comprise at least about five contiguous amino acids from the ARAg-h-1 amino acid sequence shown in FIG. 7A. Many ARAg polypeptides are encoded by nucleic acid segments that hybridize under stringent conditions to the ARAg-h-1 nucleotide sequence shown in FIG. 7A. Many ARAg polypeptides also have an antigenic determinant in common with ARAg-h-1.

Many ARAg polypeptides comprise at least one of the following domains: a signal sequence, an intracellular domain, a transmembrane domain and an extracellular domain. The extracellular domain usually comprises at least one, and sometimes seven immunoglobulin-like domains, usually of the variable type. Some ARAg polypeptides are glycosylated such that treatment with the enzyme N-glycanase causes a reduction in molecular weight from about 131 kDa to 114 kDa. Many ARAg polypeptides are characterized by their presence on the surface of alloantigen-activated $CD8^+$ T-cells, monocytes, granulocytes and peripheral dendritic cells, and their substantial absence on resting T-cells, mitogen-activated $CD8^+$ T-cells, B-cells, erythroid cell lines, myelomonocitic cell lines, EBV-LCL cell lines or fibroblastoid cell lines.

Also provided are extracellular domains of ARAg polypeptides. Usually, the extracellular domain comprises at least one immunoglobulin-like domain, and sometimes seven such domains, usually of the variable type. The extracellular domains are preferably soluble and capable of binding to an ARAg receptor.

In another aspect of the invention, antibodies that specifically bind to the ARAg-h-1 polypeptide, whose sequence is shown in FIG. 7A, are provided. Some such antibodies compete with a specific monoclonal antibody designated P1C5 for specific binding to ARAg-h-1.

The invention also provides nucleic acid fragments encoding ARAg polypeptides. Most nucleic acid fragments hybridize to the nucleic acid sequence encoding ARAg-h-1 shown in FIG. 7A under stringent conditions.

The invention also provides isolated cell lines containing nucleic acids as described above. Preferably, the cell lines express an ARAg polypeptide on their cell surface.

The invention also provides methods for screening for immunosuppressive agents. In these methods, an ARAg polypeptide is contacted with a potential immunosuppressive agent. Specific binding between the ARAg polypeptide and the potential agent is then detected indicative of immunosuppressive activity.

In another aspect of the invention, methods for screening for an ARAg receptor are provided. A biological sample containing an ARAg receptor is contacted with an ARAg polypeptide. A complex formed between the receptor and ARAg polypeptide is isolated. The complex is then dissociated to obtain the receptor.

The invention also provides methods for suppressing an immune response in a patient suffering from an immune disease or condition. In these methods, a therapeutically effective dose of a pharmaceutical composition, comprising a pharmaceutically active carrier and a monoclonal antibody against a ARAg antigen, is administered to the patient.

Also provided are methods of monitoring an immune disease or condition. In these methods, a tissue sample from the patient is contacted with a monoclonal antibody against ARAg and specific binding between the monoclonal antibody and tissue sample is detected.

BRIEF DESCRIPTION OF THE DRAWINGS

FIG. 7A: Nucleotide (upper) (SEQ. ID NO: 2) and predicted amino acid sequence (lower) (SEQ. ID NO: 3) of ARAg-h-1. An in-frame upstream termination codon (nucleotides 4–6), a predicted $NH_2$-terminal signal sequence and a transmembrane spanning domain are underlined. Potential N-glycosylation sites are double underlined. Cystsine residues are denoted by a triangle and, where applicable, numbered according to the putative immunoglobulin-like domain in which they appear.

FIG. 7B: Kyte-Doolittle hydropathy plot of the predicted ARAg-h-1 amino acid sequence.

FIG. 8: Comparison of the amino acid sequences of the seven variable-type immunoglobulin-type domains of ARAg-h-1. Domains VII, VI, V, IV, III, II and I are designated SEQ. ID NOS: 4, 5, 6, 7, 8, 9 and 10, respectively. The consensus sequence is designated SEQ. ID NO: 11.

DEFINITIONS

Figure 1:
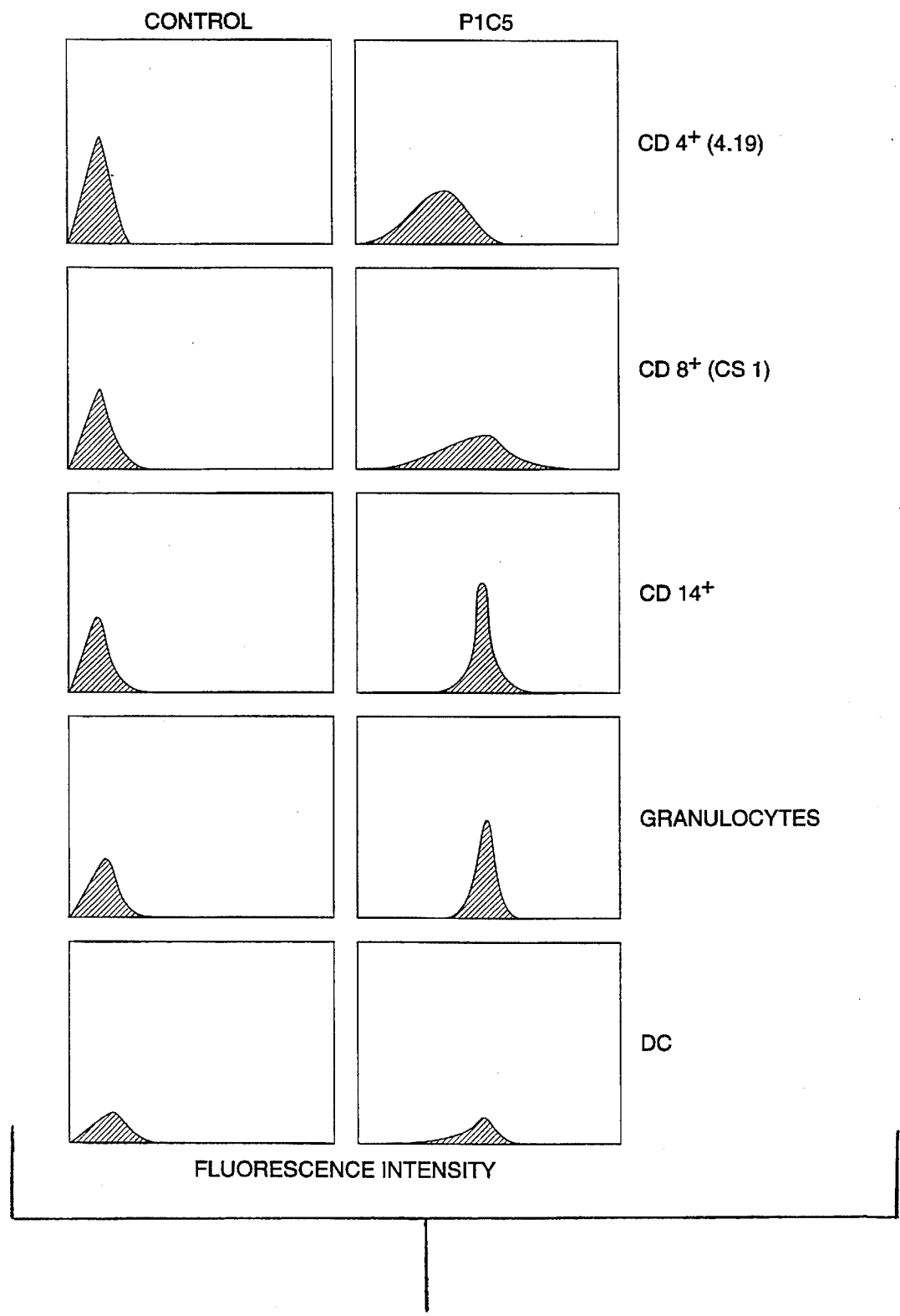
FIG. 1: FACS™ analysis of various immune cell types stained with anti-ARAg-h-1 antibody. The $CD4^+$ and $CD8^+$ cells are shown in an activated state. Other cells are fresh. DC=dendritic cell.

Abbreviations for the twenty naturally occurring amino acids follow conventional usage (*Immunology—A Synthesis*, (E. S. Golub & D. R. Gren, eds., Sinauer Associates, Sunderland, Mass., 2nd ed., 1991) (incorporated by reference for all purposes). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The phrase "polynucleotide sequence" or "nucleic acid fragment" refers to a single or double-stranded polymer of deoxyribonucleotide or ribonucleotide bases read from the 5' to the 3' end. It includes self-replicating plasmids, infectious polymers of DNA or RNA and non-functional DNA or RNA.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 7A, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. (USA)* 85:2444 (1988) (each of which is incorporated by reference for all purposes), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length ARAg-h-1 sequence shown in FIG. 7A.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "cognate" as used herein refers to a gene sequence that is evolutionarily and functionally related between species. For example, in the human genome, the human CD4 gene is the cognate gene to the mouse CD4 gene, since the sequences and structures of these two genes indicate that they are highly homologous and both genes encode a protein which functions in signaling T-cell activation through MHC class II-restricted antigen recognition. Thus, the cognate murine gene to the ARAg-h-1 gene is the murine gene which encodes an expressed protein which has the greatest degree of sequence identity to the ARAg-h-1 protein and which exhibits an expression pattern similar to that of ARAg-h-1 protein (e.g., expressed on CD8$^+$ cells in response to alloantigen but not mitogen stimulation). For example, cognate ARAg genes include: rat, rabbit, canine, nonhuman primate, porcine, murine, and hamster.

The term "substantially pure" means an object species (e.g. an ARAg polypeptide or nucleic acid fragment) is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "epitope" includes any protein determinant capable of specific binding to an immunoglobulin or T-cell receptor. Specific binding exists when the dissociation constant for antibody binding to an antigen is $\leq 1$ µM, preferably $\leq 100$ nM and most preferably $\leq 1$ nM. Epitopic determinants usually consist of chemically active surface groupings of molecules such as amino acids or sugar side chains and usually have specific three dimensional structural characteristics, as well as specific charge characteristics.

The term "patient" includes human and veterinary subjects.

DETAILED DESCRIPTION OF SPECIFIC EMBODIMENTS

I. Polypeptides of the Invention

According to one embodiment of the invention, novel cell surface antigens and fragments thereof are provided. The amino acid sequence of the first ARAg antigen to be characterized [hereinafter ARAg-h-1] is shown in FIG. 7A. The suffix "h" designates a human origin. The suffix "-1" indicates that ARAg-h-1 is the first ARAg antigen to be characterized. The term ARAg antigen refers not only to the protein having the sequence shown in FIG. 7A but also to other proteins that represent allelic, nonallelic, and cognate variants of ARAg-h-1, and natural or induced mutants of any of these. Usually, ARAg polypeptides will also show substantial sequence identity with the ARAg-h-1 sequence. The term ARAg polypeptide is used generically to encompass full-length ARAg proteins and fragments thereof. Typically, an ARAg polypeptide will contain at least 4 and more commonly 5, 6, 7, 10 or 20 or more contiguous amino acids from the ARAg-h-1 sequence. It is well known in the art that functional domains, such as binding domains or epitopes can be formed from as few as four amino acids residues.

ARAg polypeptides will typically be encoded by nucleotide sequences that exhibit substantial sequence identity with the nucleotide sequence encoding ARAg-h-1 shown in FIG. 7A. The nucleotides encoding ARAg proteins will also typically hybridize to the ARAg-h-1 sequence under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

Often, ARAg polypeptides will share at least one antigenic determinant in common with ARAg-h-1. The existence of such a common determinant is evidenced by cross-reactivity of the variant protein with any antibody prepared against ARAg-h-1 (see Section IV). Cross-reactivity is often tested using polyclonal sera against ARAg-h-1, but can also be tested using one or more monoclonal antibodies against ARAg-h-1, such as the antibody designated P1C5.

Often ARAg proteins will contain modified polypeptide backbones. Modifications include chemical derivatizations of polypeptides, such as acetylations, carboxylations and the like. They also include glycosylation modifications and processing variants of a typical polypeptide. These processing steps specifically include enzymatic modifications, such as ubiquitinization and phosphorylation. See, e.g., Hershko & Ciechanover, *Ann. Rev. Bioch.* 51:335–364 (1982) (incorporated by reference for all purposes). The ARAg-1-h protein, for example, contains seven putative glycosylation sites in its extracellular domain and several putative phosphorylation sites in its intracellular domain. The glycosylated state of the ARAg-h-1 antigen and other closely related ARAg antigens gives rise to a simple test for recognizing the antigen. Naturally occurring ARAg-h-1 or ARAg-h-1 expressed from a cloned gene in mammalian cell culture has a molecular weight of about 131 kDa. However, on treatment with N-glycanase, the molecular weight shifts to about 114 kDa. The change in molecular weight probably results from digestion of carbohydrate residues attached to some or all of the seven putative N-glycosylation sites identified on the amino acid sequence of ARAg-h-1.

Figure 9:
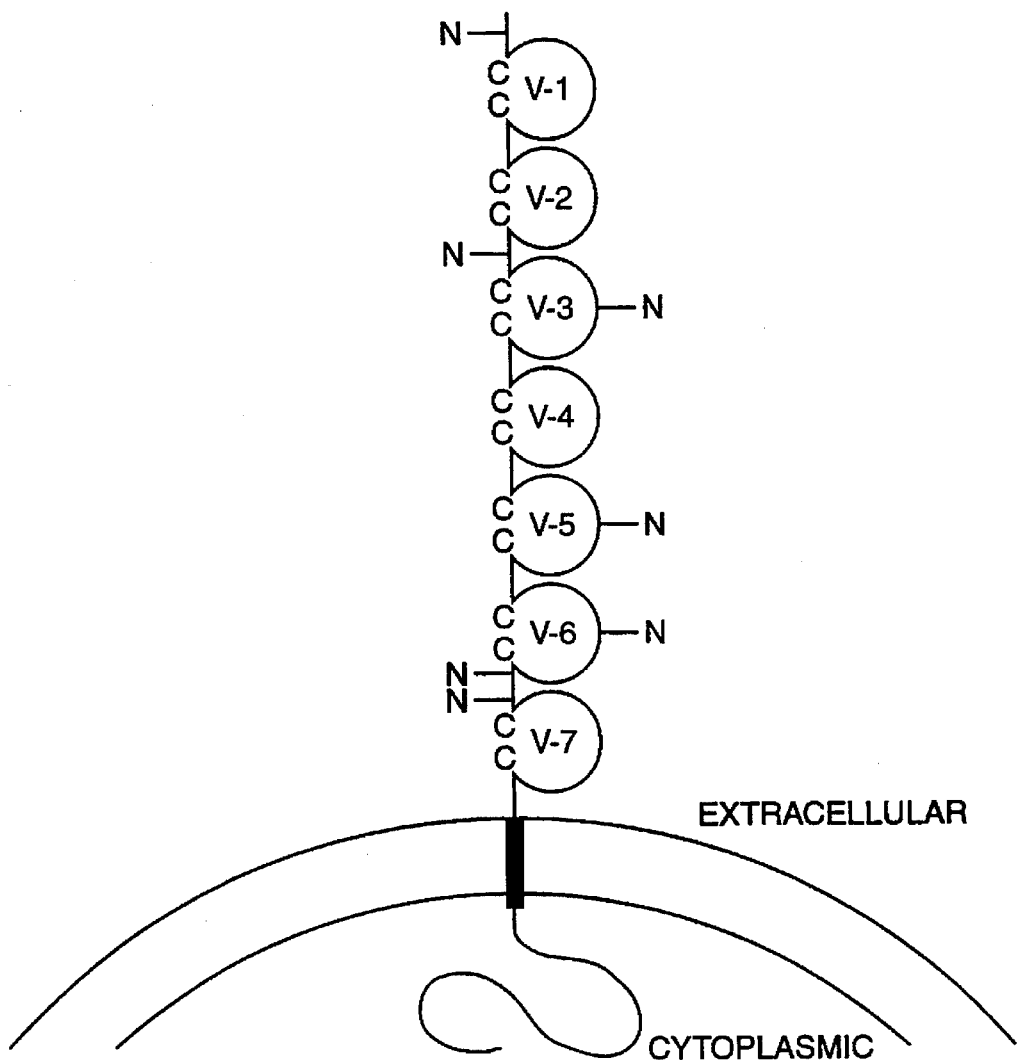
FIG. 9: Schematic representation of the domain structure of ARAg-h-1. Immunoglobulin-like domains are represented by numbered loops and the cystsine residues enclosing the loops are denoted "C." Potential N-glycoslylation sites are indicated "N." The transmembrane spanning domain is shown as a rectangle passing through the cell membrane and the cytoplasmic domain follows oriented toward the inner side of the lipid bilayer.

ARAg antigens likely share some or all of the topological features shown for ARAg-h-1 in FIG. 9. The amino acid sequence for ARAg-h-1 contains a 20 amino acid putative N-terminal signal sequence and a single additional hydrophobic stretch spanning residues 955–979. The hydrophobic stretch probably corresponds to a transmembrane domain and its existence is consistent with ARAg-h-1 being a type I integral membrane protein (i.e., having a single transmembrane domain with the N-terminal domain comprising the extracellular region and the C-terminus comprising the intracellular region). The segments of ARAg-h-1 amino-proximal to the transmembrane segment are designated the extracellular domain, while the segments carboxy-proximal to the transmembrane segment are designated the intracellular domain. From the amino-terminus, the extracellular domain has an NH$_2$-terminal hydrophobic putative signal sequence, and seven variable type immunoglobulin-like domains (designated V-1 through V-7 from N-terminal to C-terminal). The amino acids coordinates of the immunoglobulin-like domains are as follows:

V1 (aa43-121)
V2 (aa168-249)
V3 (aa304-377)
V4 (aa434-511)
V5 (aa562-640)
V6 (aa697-778)
(V7 (aa834-909)

Each Ig-like domain is enclosed by a pair of disulfide-linked cysteine residues spaced between 73 and 81 amino acids apart. The cysteine residues form a loop enclosing nine antiparallel β-strands into two β-sheets. This arrangement is typical of variable immunoglobulin domains observed in other IgSF members. The seventh immunoglobulin like domain is linked to the putative transmembrane domain, which is in turn linked to a 45 amino acid highly charged intracellular domain.

Although not all of the domains discussed above are necessarily present in all ARAg proteins, an extracellular domain is expected to be present in most. Indeed, in some ARAg proteins, it is possible that only an extracellular domain is present, and the natural state of such proteins is not as cell-surface bound proteins, but as soluble proteins, for example, dispersed in an extracellular body fluid. The existence of soluble variant forms has been observed for other immunoglobulin superfamily members, e.g., fibroblast growth factor receptor (see, e.g., Johnson et al., *Mol. Cell. Biol.* 10:4728–4736 (1990)), as well as antibodies.

The ARAg-h-1 protein is unusual in containing seven variable type Ig-like domains. No known IgSF member has more than four such domains. It is likely that other ARAg members will contain a relatively large number of variable Ig-like domains. It is particularly likely that the N-terminal domain will be a variable Ig-like domain, in keeping with the structure of other IgSF members. In IgSF proteins, which are anchored to a cell surface, the N-terminal domain is the most-externally orientated position and therefore most accessible for contact with other molecules or receptors for signal transduction.

Besides substantially full-length polypeptides, the present invention provides for biologically active fragments of the polypeptides. Significant biological activities include receptor binding, antibody binding (e.g., the fragment competes with a full-lengthARAg polypeptide for specific binding to an antibody), immunogenicity (i.e., possession of epitopes that stimulate B or T-cell responses against the fragment), and agonism or antagonism of the binding of ARAg to its receptor. A segment of an ARAg protein will ordinarily comprise at least about 5 contiguous amino acids, typically at least about 7 contiguous amino acids, more typically at least about 9 contiguous amino acids, usually at least about 11 contiguous amino acids, preferably at least about 13 contiguous amino acids, more preferably at least about 16 contiguous amino acids, and most preferably at least about 20, 30, 50, 75, 100 or 125 contiguous amino acids. Segments of a particular domain will be segments of the appropriate size within the corresponding domain. A full-length extracellular domain is the complete fraction of an ARAg polypeptide that is external to the cellular membrane, that is, the portion of the ARAg polypeptide toward the amino terminal side of the transmembrane domain.

Segments of ARAg proteins are often terminated near boundaries of functional or structural domains. Structural and functional domains are identified by comparison of nucleotide and/or amino acid sequence data such as is shown in FIG. 7A, to public or proprietary sequence databases. Preferably, computerized comparison methods are used to identify sequence motifs or predicted protein conformation domains that occur in other proteins of known structure and/or function. Structural domains include an intracellular domain, transmembrance domain, and extracellular domain, which is in turn subdivided into from one to seven immunoglobulin type domains. Functional domains include an extracellular binding domain through which the ARAg protein interacts with external soluble molecules or other cell-bound ligands and an intracellular signal-transducing domain.

Some fragments will contain only extracellular domains, such as one or more immunoglobulin like domains. Such fragment will often retain the binding specificity of an intact ARAg protein, but will be soluble rather than membrane bound. Such fragments are useful as competitive inhibitors of ARAg binding.

ARAg antigens are also identified by a characteristic cellular distribution. Most notably, ARAg antigens are easily detected on long-term activated T-cells (more so on $CD8^+$ than $CD4^+$ cells), monocytes, granulocytes and peripheral dendritic cells, (mean channel fluorescence usually $\geq 3$, and often $\geq 5$, on a Coulter Profile Flow Cytometer after immunofluoroescense staining) and are substantially absent (mean channel fluorescence usually <3 and often $\leq 1$) on resting T-cells, erythroid cell lines, certain myelomonocytic cell lines, EBV-LCL cell lines and fibroblastoid cell lines. The term alloantigen-activated T-cell denotes a T-cell culture or clone that has been propagated by stimulating with cells from another individual from the same species. Usually the stimulating cells have had their proliferative potential nullified by irradiation. The term mitogen-stimulated T-cell denotes a T-cell culture or clone that has been propagated by stimulation with a mitogen, such as PHA, ConA, OKT3 or PMA. The requirement for an extensive period of exposure to alloantigens (5 days) or mitogens (3–4 weeks) for significant expression of ARAg proteins suggests that ARAg should be classified as a very late activation antigen. The expression of ARAg on T-cells within one week of exposure to allogenic, but not mitogenic stimulation differs from most, if not all, other very late activation antigens. Stimuli such as PHA and ConA, which fail to induce the expression of P1C5 on T-cells, do induce the expression of activation markers such as CD25, CD71 and CD69. However, Wadsworth et al., *J. Immunol.* 149:421–428 (1992), have reported identification of a very late activation murine antigen which apparently is not expressed after culture with IL-2 for up to 10 weeks.

ARAg antigens are further defined by their role in proliferation of certain cell types. Example 4 shows that an anti-ARAg-h-1 antibody has the capacity to block proliferation of certain T-cells in some circumstances. Specifically, anti-ARAg antibody inhibits the proliferative response of $CD8^+$ T-cells but not that of $CD4^+$ cells induced by allogeneic B-cells. The antibody also inhibits the proliferative response of $CD4^+$ T-cells incubated with allogeneic monocytes.

II. Methods of producing polypeptides

A. Recombinant Technologies

The nucleotide and amino acid sequences of ARAg-h-1 shown in FIG. 7A, and corresponding sequences for other ARAg variants obtained as described in Section III, allow production of polypeptides of full-length ARAg polypeptide sequences and fragments thereof. Such polypeptides may be produced in prokaryotic or eukaryotic host cells by expression of polynucleotides encoding ARAg, or fragments and analogs thereof. The cloned DNA sequences are expressed in hosts after the sequences have been operably linked to (i.e., positioned to ensure the functioning of) an expression control sequence in an expression vector. Expression vectors are typically replicable in the host organisms either as episomes or as an integral part of the host chromosomal DNA. Commonly, expression vectors will contain selection markers, e.g., tetracycline resistance or hygromycin resistance, to permit detection and/or selection of those cells transformed with the desired DNA sequences (see, e.g., U.S. Pat. No. 4,704,362).

E. coli is one prokaryotic host useful for cloning the DNA sequences of the present invention. Other microbial hosts suitable for use include bacilli, such as Bacillus subtilis, and other Enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired. Insect cells with appropriate vectors, usually derived from the SF9 baculovirus, are also suitable for expressing ARAg peptides. See Luckow, et al. Bio/Technology 6:47–55 (1988).

Higher eukaryotic mammalian tissue cell culture may also be used to express and produce the polypeptides of the present invention (see Winnacker, From Genes to Clones (VCH Publishers, NY, N.Y., 1987)) (incorporated by reference for all purposes). Eukaryotic cells are actually preferred, because a number of suitable host cell lines capable of secreting and authentically modifying human proteins have been developed in the art, and include the CHO cell lines, various COS cell lines, HeLa cells, myeloma cell lines, Jurkat cells, etc. Expression vectors for these cells can include expression control sequences, such as an origin of replication, a promoter (e.g., a HSV tk promoter or pgk (phosphoglycerate kinase) promoter), an enhancer (Queen et al., Immunol. Rev. 89:49 (1986)), and necessary processing information sites, such as ribosome binding sites, RNA splice sites, polyadenylation sites (e.g., an SV40 large TAg poly A addition site), and transcriptional terminator sequences. Preferred expression control sequences are promoters derived from immunoglobulin genes, SV40, adenovirus, bovine papillomavirus, and the like. The vectors containing the DNA segments of interest (e.g., polypeptides encoding a ARAg polypeptide) can be transferred into the host cell by well-known methods, which vary depending on the type of cellular host. For example, $CaCl_2$ transfection is commonly utilized for prokaryotic cells, whereas $CaPO_4$ treatment or electroporation may be used for other cellular hosts. Vectors may exist as episome or integrated into the host chromosome.

B. Naturally Occurring ARAg Proteins

Natural ARAg polypeptides are isolated by conventional techniques such as affinity chromatography. For example, polyclonal or monoclonal antibodies are raised against previously-purified ARAg-h-1 and attached to a suitable affinity column by well known techniques. See, e.g., Hudson & Hay, Practical Immunology (Blackwell Scientific Publications, Oxford, UK, 1980), Chapter 8 (incorporated by reference for all purposes). For example, anti-ARAg can be immobilized to a protein-A sepharose column via crosslinking of the $F_c$ domain with a homobifunctional crosslinking agent, such as dimethyl pimelimidate. Cell extracts are then passed through the column, and ARAg protein specifically bound by the column, eluted with, for example, 0.5M pyrogenic acid, pH 2.5. Usually, an intact form of ARAg is obtained by such isolation techniques. Peptide fragments are generated from intact ARAg by chemical (e.g., cyanogen bromide) or enzymatic cleavage (e.g., V8 protease or trypsin) of the intact molecule.

C. Other Methods

Alternatively, ARAg polypeptides can be synthesized by chemical methods or produced by in vitro translation systems using a polynucleotide template to direct translation. Methods for chemical synthesis of polypeptides and in vitro translation are well known in the art, and are described further by Berger & Kimmel, Methods in Enzymology, Volume 152, Guide to Molecular Cloning Techniques Academic Press, Inc., San Diego, Calif., 1987) (incorporated by reference for all purposes).

III. Nucleic Acids

A. Cloning ARAg nucleic acids

Example 9 presents nucleic acid sequence data for a cDNA clone of an ARAg antigen designated ARAg-h-1. This sequence data can be used to design probes with which to isolate other ARAg genes. These genes include the human genomic gene encoding ARAg-h-1, cognate cDNA and genomic clones from other species, and allelic and nonallelic variants of all of these genes. Specifically, all nucleic acids encoding all ARAg polypeptides disclosed in this application are provided. Genomic libraries of many species are commercially available (e.g., Clontech, Palo Alto, Calif.), or can be isolated de novo by conventional procedures. cDNA libraries are best prepared from cells of the types found to express ARAg-h-1 in large amounts, such as alloantigen activated $CD8^+$ T-lymphocytes, monocytes and granulocytes.

The probes used for isolating clones typically comprise a sequence of about at least 24 contiguous nucleotides (or their complement) of the cDNA sequence shown in FIG. 7A. For example, a full-length polynucleotide corresponding to the sequence of FIG. 7A may be labeled and used as a hybridization probe to isolate genomic clones from a human genomic clone library in e.g., λEMBL4 or λGEM11 (Promega Corporation, Madison, Wis.); typical hybridization conditions for screening plaque lifts (Benton & Davis, Science 196:180 (1978)) can be: 50% formamide, 5×SSC or SSPE, 1–5×Denhardt's solution, 0.1–1% SDS, 100–200 μg sheared heterologous DNA or tRNA, 0–10% dextran sulfate, $1\times10^5$ to $1\times10^7$ cpm/ml of denatured probe with a specific activity of about $1\times10^8$ cpm/μg, and incubation at 42° C. for about 6–36 hours. Prehybridization conditions are essentially identical except that probe is not included and incubation time is typically reduced. Washing conditions are typically 1–3×SSC, 0.1–1% SDS, 50°–70° C. with change of wash solution at about 5–30 minutes. Hybridization and washing conditions are typically less stringent for isolation of cognate or nonallelic variants than for e.g., the human genomic clone of ARAg-h-1.

Alternatively, probes can be used to clone ARAg genes by methods employing the polymerase chain reaction (PCR).

Methods for PCR amplification are described in e.g., *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19:4967 (1991); Eckert, K. A. and Kunkel, T. A., *PCR Methods and Applications* 1:17 (1991); PCR (eds. McPherson et al., IRL Press, Oxford); and U.S. Pat. No. 4,683,202 (each of which is incorporated by reference for all purposes).

Alternatively, synthetic polynucleotide sequences corresponding to all or part of the sequences shown in FIG. 7A may be constructed by chemical synthesis of oligonucleotides.

Nucleotide substitutions, deletions, and additions can be incorporated into the polynucleotides of the invention. Nucleotide sequence variation may result from degeneracy of the genetic code, from sequence polymorphisms of various ARAg-h-1 alleles, minor sequencing errors, or may be introduced by random mutagenesis of the encoding nucleic acids using irradiation or exposure to EMS, or by changes engineered by site-specific mutagenesis or other techniques of modern molecular biology. See Sambrook et al., *Molecular Cloning: A Laboratory Manual* (C.S.H.P. Press, NY 2d ed., 1989) (incorporated by reference for all purposes). For nucleotide sequence that are capable of being transcribed and translated to produce a functional polypeptide, degeneracy of the genetic code results in a number of nucleotide sequences that encode the same polypeptide. The invention includes all such sequences. Generally, nucleotide substitutions, deletions, and additions should not substantially disrupt the ability of an ARAg polynucleotide to hybridize to the sequence of ARAg-h-1 shown in FIG. 7A under stringent conditions. Typically, ARAg polynucleotides comprise at least 25 consecutive nucleotides which are substantially identical to a naturally-occurring ARAg sequence (e.g., FIG. 7A), more usually ARAg polynucleotides comprise at least 50 to 100 consecutive nucleotides which are substantially identical to a naturally-occurring ARAg sequence.

ARAg polynucleotides may be short oligonucleotides (e.g., 25–100 bases long), such as for use as hybridization probes and PCR (or LCR) primers. ARAg polynucleotide sequences may also comprise part of a larger polynucleotide that includes sequences that facilitate transcription (expression sequences) and translation of the coding sequences, such that the encoded polypeptide product is produced. Construction of such polynucleotides is well known in the art and is described further in Sambrook et al., supra. The ARAg polynucleotide and may be fused in frame with another polynucleotide sequence encoding a different protein (e.g., glutathione S-transferase, β-galactosidase or an immunoglobulin FC domain) for encoding expression of a fusion protein (see, e.g., Byrn et al., *Nature*, 344:667–670 (1990)) (incorporated by reference for all purposes).

IV. Antibodies

In another embodiment of the invention, antibodies against ARAg and to its receptor (see Section V) are provided.

A. General Characteristics of Antibodies

Antibodies or immunoglobulins are typically composed of four covalently bound peptide chains. For example, an IgG antibody has two light chains and two heavy chains. Each light chain is covalently bound to a heavy chain. In turn each heavy chain is covalently linked to the other to form a "Y" configuration, also known as an immunoglobulin conformation. Fragments of these molecules, or even heavy or light chains alone, may bind antigen. Antibodies, fragments of antibodies, and individual chains are also referred to herein as immunoglobulins.

A normal antibody heavy or light chain has an N-terminal ($NH_2$) variable (V) region, and a C-terminal (—COOH) constant (C) region. The heavy chain variable region is referred to as $V_H$ (including, for example, $V_\mu$), and the light chain variable region is referred to as $V_L$ (including $V_\kappa$ or $V_\lambda$). The variable region is the part of the molecule that binds to the antibody's cognate antigen, while the Fc region (the second and third domains of the C region) determines the antibody's effector function (e.g., complement fixation, opsonization). Full-length immunoglobulin or antibody "light chains" (generally about 25 KDa, about 214 amino acids) are encoded by a variable region gene at the N-terminus (generally about 110 amino acids) and a κ (kappa) or λ (lambda) constant region gene at the COOH-terminus. Full-length immunoglobulin or antibody "heavy chains" (generally about 50 KDa, about 446 amino acids), are similarly encoded by a variable region gene (generally encoding about 116 amino acids) and one of the constant region genes, e.g., gamma (encoding about 330 amino acids). Typically, the "$V_L$" will include the portion of the light chain encoded by the $V_L$ and/or $J_L$ (J or joining region) gene segments, and the "$V_H$" will include the portion of the heavy chain encoded by the $V_H$, and/or $D_H$ (D or diversity region) and $J_H$ gene segments. See, generally, Roitt et al., *Immunology* (2d ed. 1989), Chapter 6 and Paul, *Fundamental Immunology* (Raven Press, 2d ed., 1989) (incorporated by reference for all purposes).

An immunoglobulin light or heavy chain variable region consists of a "framework" region interrupted by three hypervariable regions, also called complementarity-determining regions or CDRs. The extent of the framework region and CDRs have been defined (see Kabat et al. (1987), "Sequences of Proteins of Immunological Interest," U.S. Department of Health and Human Services; Chothia et al., *J. Mol. Biol.* 196:901–917 (1987)) (incorporated by reference for all purposes). The sequences of the framework regions of different light or heavy chains are relatively conserved within a species. The framework region of an antibody, that is the combined framework regions of the constituent light and heavy chains, serves to position and align the CDRs in three dimensional space. The CDRs are primarily responsible for binding to an epitope of an antigen. The CDRs are typically referred to as CDR1, CDR2, and CDR3, numbered sequentially starting from the N-terminus.

The two types of light chains, κ and λ, are referred to as isotypes. Isotypic determinants typically reside in the constant region of the light chain, also referred to as the $C_L$ in general, and $C_\kappa$ or $C_\lambda$ in particular. Likewise, the constant region of the heavy chain molecule, also known as $C_H$, determines the isotype of the antibody. Antibodies are referred to as IgM, IgD, IgG, IgA, and IgE depending on the heavy chain isotype. The isotypes are encoded in the mu (μ), delta (Δ), gamma (γ), alpha (α), and epsilon (ε) segments of the heavy chain constant region, respectively. In addition, there are a number of γ subtypes.

The heavy chain isotypes determine different effector functions of the antibody, such as opsonization or complement fixation. In addition, the heavy chain isotype determines the secreted form of the antibody. Secreted IgG, IgD, and IgE isotypes are typically found in single unit or monomeric form. Secreted IgM isotype is found in pentameric form; secreted IgA can be found in both monomeric and dimeric form.

B. production of Antibodies

Antibodies which bind either an ARAg antigen, a receptor thereto, or binding fragments of either, can be produced by a variety of means. The production of non-human monoclonal antibodies, e.g., murine, rat and so forth, is well known and may be accomplished by, for example, immunizing the animal with a preparation containing ARAg or its receptor, or a fragment of either of these. Antibody-producing cells obtained from the immunized animals are immortalized and screened for the production of an antibody which binds to ARAg or its receptor. See Harlow & Lane, *Antibodies, A Laboratory Manual* (C.S.H.P. NY, 1988) (incorporated by reference for all purposes).

Techniques for generation of human monoclonal antibodies have also been described but are generally more onerous than murine techniques and not applicable to all antigens. See, e.g., Larrick et al., U.S. Pat. No. 5,001,065, for review (incorporated by reference for all purposes). An alternative approach is the generation of humanized antibodies by linking the CDR regions of non-human antibodies to human constant regions by recombinant DNA techniques. See Queen et al., *Proc. Natl. Acad. Sci. USA* 86:10029–10033 (1989) and WO 90/07861 (incorporated by reference for all purposes). Alternatively, one may isolate DNA sequences which encode a human monoclonal antibody or a binding fragment thereof by screening a DNA library from human B cells according to the general protocol outlined by Huse et al., *Science* 246:1275–1281 (1989) and then cloning and amplifying the sequences which encode the antibody (or binding fragment) of the desired specificity. The protocol described by Huse is rendered more efficient in combination with phage display technology. See, e.g., Dower et al., WO 91/17271 and McCafferty et al., WO 92/01047 (each of which is incorporated by reference for all purposes). Phage display technology can also be used to mutagenize CDR regions of antibodies previously shown to have affinity for ARAg-antigens or their receptors. Antibodies having improved binding affinity are selected.

Antibodies isolated by the above procedures can be used to generate anti-idiotypic antibodies by, for example, immunization of an animal with the primary antibody. For anti-ARAg antibodies, anti-idiotype antibodies whose binding to the primary antibody is inhibited by ARAg or fragments thereof are selected. Because both the anti-idiotypic antibody and the ARAg or fragments thereof bind the primary immunoglobulin, the anti-idiotypic immunoglobulin may represent the "internal image" of an epitope and thus may substitute for the ARAg receptor.

C. Uses of Antibodies

Anti-ARAg antibodies are useful for screening cDNA expression libraries, preferably containing human or murine cDNA derived from various tissues and for identifying clones containing cDNA inserts, which encode structurally-related, immunocrossreactive proteins. See Aruffo & Seed, *Proc. Natl. Acad. Sci. USA* 84:8573–8577 (1987) (incorporated by reference for all purposes). Antibodies are also useful to identify and/or purify immunocrossreactive proteins that are structurally or evolutionarily related to the native ARAg protein or to fragments thereof used to generate the antibody. Diagnostic and therapeutic uses of antibodies and idiotypic antibodies are described in Section VII, infra.

V. ARAg Receptor

The term ARAg receptor is used to denote a protein that specifically binds to an ARAg polypeptide and which is capable of forming a complex with such polypeptide, at least in part, by noncovalent binding. Receptors may be naturally-occurring or synthetic molecules, and may be in soluble form or anchored to the surface of a cell. The term "ARAg receptor" does not usually include antibodies to ARAg polypeptides. Usually, binding of ARAg to its receptor will initiate a signal that alters the physical and/or functional phenotype of a cell bearing the ARAg antigen and/or a cell bearing the ARAg receptor. Antibodies against either ARAg or its receptor may have the capacity to block signal transduction. It will, of course, be recognized that the designation of ARAg as a "ligand" and its specific binding partner as a "receptor" is somewhat arbitrary and could be reversed in some circumstances.

Cells expressing the ARAg receptor are identified by screening different cell types from, such as those listed in Table 1, particularly lymphoid and hematopoietic cells, using labelled ARAg, preferably in soluble form, as a probe. The cells can be from any mammalian species. ARAg receptor polypeptides are then purified from cells identified by this screening method using techniques of classical protein chemistry. Such techniques include selective precipitation with such substances as ammonium sulfate, column chromatography, immunopurification methods, and others. See, e.g., R. Scopes, *Protein Purification: Principles and Practice* (Springer-Verlag, NY, 1982) (incorporated by reference for all purposes). Usually, purification procedures will include an affinity chromatography step in which ARAg protein or a binding fragment thereof is used as the immobilized reagent. ARAg receptors may also be purified using anti-idiotypic antibodies to ARAg as the affinity reagent.

To determine the amino acid sequence or to obtain polypeptide fragments of the receptor, the receptor may be digested with trypsin. Peptide fragments may be separated by reversed-phase high performance liquid chromatography (HPLC) and analyzed by gas-phase sequencing. Other sequencing methods known in the art may also be used. The sequence data can be used to design degenerate probes for isolation of cDNA or genomic clones encoding ARAg receptors. Alternatively, cDNA clones encoding ARAg receptors can be obtained by expression cloning. In this approach, a cDNA library is prepared from cells expressing the ARAg receptor (identified as discussed, supra). The library is expressed in appropriate cells (e.g., COS-7), and clones bearing the ARAg receptor identified by screening with labelled ARAg, preferably in soluble form.

The ARAg receptors or the specific external regions of the receptors may be used to affinity purify respective ARAgs. ARAg receptors and binding fragments thereof are also useful as agonists or antagonists of ARAg receptor binding, and can be used in the therapeutic methods discussed in Section VII, infra. Often binding fragments will comprise part of the extracellular domain of an ARAg receptor. ARAg receptors and fragments thereof are also useful in screening assays for identifying agonists and antagonists of ARAg and/or the ARAg receptor.

VI. Screening for Agonists and Antagonists of ARAg.

ARAg and ARAg receptor fragments, analogs thereof, antibodies and anti-idiotypic antibodies thereto, as well as other chemical or biological agents are screened for their ability to block or enhance binding of an ARAg antigen to its receptor. In addition, they are tested for their ability to stimulate or inhibit metabolic processes, such as DNA synthesis or protein phosphorylation in cells bearing either an ARAg antigen or an ARAg receptor anchored to their surfaces.

In some methods, the compound under test is screened for its ability to block or enhance binding of a purified binding fragment of ARAg antigen to a purified binding fragment of the ARAg receptor. In such experiments, either the ARAg antigen fragment or its receptor is usually immobilized to a solid support. The test compound then competes with an ARAg or ARAg receptor fragment (whichever is not attached to the support) for binding to the support. Usually, either the test compound or the competing ligand is labelled.

In other methods, either or both of the ARAg antigen and ARAg receptor, or binding fragments of these molecules, are expressed on a cell surface. For example, ARAg-h-1 antigen is expressed from recombinant DNA in COS-7 cells (see Example 7). In these methods, the existence of agonism or antagonism is determined from the degree of binding between ARAg and its receptor that occurs in the presence of the test compound. Alternatively, activity of the test compound is assayed by measurement of $^3$H-thymidine incorporation into DNA or $^{32}$P incorporation into proteins in cells bearing an ARAg polypeptide and/or cells bearing an ARAg receptor.

Compounds that block ARAg-induced DNA synthesis or protein phosphorylation are antagonists. Compounds that activate DNA synthesis or phosphorylation via interaction with ARAg or its receptor are agonists. Agonistic or antagonistic activity may also be determined from other functional or physical endpoints of leukocyte activation, such as monocyte chemotaxis, opsonization, or oxidative burst, or from clinically desirable or undesirable outcomes, such as cytolytic activity, or extravasation of ARAg$^+$ leukocytes into tissues from blood vessels.

The ability of agents to agonize or antagonize T-cell proliferation in vitro can be correlated with the ability to affect the immune response in vivo. In vivo activity is typically assayed using suitable animal models such as mice or rats. To assay the effect of agents on allograft rejection, for example, potential therapeutic agents can be administered to the animals at various times before introduction of the allogeneic tissue; and the animals can be monitored for graft rejection. Suitable methods for performing the transplant and monitoring for graft rejection have been described (see, e.g., Hislop et al., *J. Thorac. Cardiovasc.* 100:360–370 (1990)) (incorporated by reference for all purposes).

VII. Therapeutic and Diagnostic Methods and Compositions

A. Diagnostic Methods

Diseases and conditions of the immune system associated with an altered abundance, or functional mutation, of ARAg protein or mRNA may be diagnosed using the probes and/or antibodies of the present invention. The efficacy of therapeutic agents in treating such diseases and conditions can be monitored. Such diseases and conditions include transplant rejection, graft versus host disease, autoimmune diseases and inflammation.

Diagnosis can be accomplished by removing a cellular sample (e.g., blood sample, lymph node biopsy or tissue) from a patient. The sample is then subjected to analysis for determining: (1) the amount of expressed ARAg antigen in individual cells of the sample (e.g., by immunohistochemical staining of fixed cells with an anti-ARAg antibody or FACS™ analysis), (2) the amount of ARAg mRNA in individual cells (by in situ hybridization with a labelled ARAg polynucleotide probe), (3) the amount of ARAg mRNA in the cellular sample by RNA extraction followed by hybridization to a labeled ARAg polynucleotide probe (e.g., by Northern blotting, dot blotting, solution hybridization or quantitative PCR), or (4) the amount of ARAg protein in the cellular sample (e.g., by cell disruption followed by immunoassay or Western blotting of the resultant cell extract).

Diagnosis can also be achieved by in vivo administration of a diagnostic reagent (e.g., a labelled anti-ARAg antibody for diagnosis of ARAg-bearing cells) and detection by in vivo imaging. The concentration of diagnostic agent administered should be sufficient that the binding to those cells have the target antigen is detectable compared to the background signal. Further, it is desirable that the diagnostic reagent can be rapidly cleared from the circulatory system in order to give the best target-to-background signal ratio. The diagnostic reagent can be labelled with a radioisotope for camera imaging, or a paramagnetic isotope for magnetic resonance or electron spin resonance imaging.

A change (typically an increase) in the level of ARAg protein or mRNA in a cellular sample from an individual, which is outside the range of clinically established normal levels, may indicate the presence of an undesirable immune reaction in the individual from whom the sample was obtained, and/or indicate a predisposition of the individual for developing (or progressing through) such a reaction. ARAg protein or mRNA levels may be employed as a differentiation marker to identify and type cells of certain lineages and developmental origins. Such cell-type specific detection may be used for histopathological diagnosis of undesired immune responses.

B. Pharmaceutical Compositions

The pharmaceutical compositions used for prophylactic or therapeutic treatment comprise an active therapeutic agent, for example, an ARAg protein, an ARAg receptor, fragments thereof, and antibodies and idiotypic antibodies thereto, and a variety of other components. The preferred form depends on the intended mode of administration and therapeutic application. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

C. Therapeutic Methods

The therapeutic methods employ the therapeutic agents discussed above for treatment of various diseases in humans or animals, particularly vertebrate mammals. The therapeutic agents include ARAg antigens, binding fragments thereof, ARAg receptors, binding fragments thereof, anti-ARAg and anti-ARAg receptor antibodies and anti-idiotypic antibodies thereto, and binding fragments of these antibodies. Some therapeutic agents function by blocking or otherwise antagonizing the action of ARAg with its receptor. Other therapeutic agents function as agonists of this interaction. Still other therapeutic agents function by killing cells bearing an ARAg antigen or receptor.

1. Dosages and Methods of Administration

In therapeutic applications, a pharmaceutical composition (e.g., comprising an anti-ARAg antibody) is administered, in vivo or ex vivo, to a patient already suffering from an undesirable immune response (e.g., transplant rejection), in an amount sufficient to cure, partially arrest, or detectably slow the progression of the condition, and its complications. An amount adequate to accomplish this is defined as a "therapeutically effective dose" or "efficacious dose." Amounts effective for this use will depend upon the severity of the condition, the general state of the patient, and the route of administration, and combination with other immunosuppressive drugs, if any, but generally range from about 10 ng to about 1 g of active agent per dose, with single dosage units of from 10 mg to 100 mg per patient being commonly used. Pharmaceutical compositions can be administered systemically by intravenous infusion, or locally by injection. The latter is particularly useful for localized undesired immune response such as host versus graft rejection. For a brief review of methods for drug delivery, see Langer, *Science* 249:1527–1533 (1990) (incorporated by reference for all purposes).

In prophylactic applications, pharmaceutical compositions are administered to a patients at risk of, but not already suffering an undesired immune reaction (e.g., a patient about to undergo transplant surgery). The amount of antibody to be administered is a "prophylactically effective dose," the precise amounts of which will depend upon the patient's state of health and general level of immunity, but generally range from 10 ng to 1 g per dose, especially 10 mg to 100 mg per patient.

Because the therapeutic agents of the invention are likely to be more selective and generally less toxic than conventional immunomodulating agents, they will be less likely to cause the side effects frequently observed with the conventional agents. Moreover, because some of the therapeutic agents are human protein sequences (e.g., binding fragments of an ARAg antigen or receptor), they are less likely to cause immunological responses such as those observed with murine anti-CD3 antibodies. The therapeutic agents of the present invention can also be combined with traditional therapeutics, and can be used to lower the dose of such agents to levels below those associated with side effects. For example, other immunosuppressive agents such as antibodies to the α3 domain, T-cell antigens (e.g., OKT4 and OKT3), antithymocyte globulin, as well as chemotherapeutic agents such as cyclosporine, glucocorticoids, azathioprine, prednisone can be used in conjunction with the therapeutic agents of the present invention.

For destruction of a specific population of target cells, it can be advantageous to conjugate the therapeutic agents of the present invention to another molecule. For example, the agents can be joined to liposomes containing particular immunosuppressive agents, to a specific monoclonal antibody or to a cytotoxin or other modulator of cellular activity, whereby binding of the conjugate to a target cell population will result in alteration of that population. For example, a number of protein toxins are well known in the art including ricin, diphtheria, gelonin, Pseudomonas toxin, and arbrin. Chemotherapeutic agents include, for example, doxorubicin, daunorubicin, methotrexate, cytotoxin, and anti-sense RNA. Antibiotics can also be used. In addition, radioisotopes such as yttrium-90, phosphorus-32, lead-212, iodine-131, or palladium-109 can be used. The emitted radiation destroys the targeted cells.

2. Diseases and Conditions Amenable to Treatment

The pharmaceutical compositions discussed above are suitable for treating several diseases and conditions of the immune system.

a. Transplant Rejection

Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individual from the same species), the host immune system is likely to mount an immune response to foreign antigens in the transplant (host-versus-graft disease) leading to destruction of the transplanted tissue. $CD8^+$ cells, $CD4^+$ cells and monocytes are all involved in the rejection of transplant tissues. The therapeutic agents of the present invention are useful, inter alia, to block alloantigen-induced immune responses in the donee (e.g., allogen-activation of $CD8^+$ T-cells and/or $CD4^+$ T-cells and/or phagocytosis by monocyte-derived cells), thereby preventing such cells from participating in the destruction of the transplanted tissue or organ.

b. Graft Versus Host Disease

A related use for the therapeutic agents of the present invention is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bond marrow transplantation; but less severe GVHD has also been reported in other cases as well, including heart and liver transplants. The therapeutic agents of the present invention are used, inter alia, to block activation of the donor T-cells e.g., via an ARAg antigen, thereby interfering with their ability to lyse target cells in the host.

c. Autoimmune diseases

A further situation in which immune suppression is desirable is in treatment of autoimmune diseases such as insulin-dependent diabetes mellitus, multiple sclerosis, stiff man syndrome, rheumatoid arthritis, myasthenia gravis and lupus erythematosus. In these disease, the body develops a cellular and/or humoral immune response against one of its own antigens leading to destruction of that antigen, and potentially crippling and/or fatal consequences. Autoimmune diseases are treated by administering one of the therapeutic agents of the invention. Optionally, the autoantigen, or a fragment thereof, against which the autoimmune disease is targeted can be administered shortly before, concurrently with, or shortly after the immunosuppressive agent. In this manner, tolerance can be induced to the autoantigen under cover of the suppressive treatment, thereby obviating the need for continued immunosuppression. See, e.g., Cobbold et al., WO 90/15152 (1990) (incorporated by reference for all purposes).

d. Inflammation

Inflammation represents the consequence of capillary dilation with accumulation of fluid and migration of phagocytic leukocytes, such as granulocytes and monocytes. Inflammation is important in defending a host against a variety of infections but can also have undesirable consequences in inflammatory disorders, such as anaphylactic shock, arthritis and gout. In response to any type of infection or inflammation, granulocytes and monocytes are induced to express a number of specific cells surface molecules termed homing receptors. The cell migrates to areas of inflammation in response to chemoattractant factors, such as certain bacterial products, complement components and so forth. Once in an area of inflammation or infection, granulocytes and monocytes establish a firm to attachment to the target endothelial cells via the homing receptor. Because homing receptors identified so far include a number of very late activation antigens, it is possible that ARAg might have this function. Accordingly, administration of therapeutic agents of the invention to block, or otherwise prevent, the interaction of ARAg with its receptor may be of value in treating inflammatory disorders.

EXAMPLES

EXAMPLE 1

Isolation of a Monoclonal Antibody Against ARAg

Female Balb/c mice were serially immunized with a long-term human alloactivated $CD3^+$, $CD4^-$, $CD8^+$ noncytolytic T-cell clone designated CS1. CS1 was derived by in vitro stimulation of CD8+ T-cells from a healthy adult (peripheral blood). Cells were stimulated by autologous activated CD4+ T-cells in conditioned medium containing a mixture of cytokines. Splenocytes from immunized mice were fused with Sp 2/0 myeloma cells and hybridomas secreting antibodies specific for the t cell clone were selected. The hybridomas were cloned by limiting dilution four times. A monoclonal antibody, designated P1C5, produced by one of the resulting hybridoma, was selected for further characterization. The PIC-5 antibody was found to have an IgG1 isotype.

EXAMPLE 2

Distribution of Antigen (ARAg-h-1) Recognized by PIC-5 Monoclonal Antibody on Different Cell Types A. Isolation of Cell Types Peripheral blood mononuclear cells (PBMC) were isolated by Ficoll-Hypaque gradient centrifugation from healthy adult volunteers (Stanford Medical School Blood Center, Stanford, Calif.). Adherent cells were eliminated by passage over nylon wool and incubation in a plastic flask overnight at 37° C. E-rosette+ cells (T-cells) were separated from E− (non-T-cells) by a single-step sheep erythrocyte rosetting procedure using neuraminidase-treated SRBC (see Engleman et al., *J. Immunol.* 127:2124 (1981) (incorporated by reference for all purposes). CD4+ or CD8+ T-cells were panned from the E+-enriched fraction. Id. Each population was more than 90% pure assayed by FACS™ analysis. The cells were then resuspended in RPMI 1640 (Bio Whittaker, Walkersville, Mass.) supplemented with 10% heat-inactivated pooled human serum, 2 mM L-glutamine, 100 μg/ml penicillin, 100 μg/ml streptomycin and 25 mm HEPES (a complete medium).

For preparation of monocytes (CD14+), PBMC were resuspended in $Mg^{2+}/Ca^{2+}$-free DPBS (Bio Whittaker, Walkersville, Mass.) containing 5% heat-inactivated human serum, and layered over a four-step gradient composed of 75%, 50%, 40%, 30% Percoll (Pharmacia LKB, Uppsala, Sweden) as previously described (Mancowitz et al., *J. Clin. Invest.* 85:955–961 (1990)). The low density fraction was collected and washed twice with 5% human serum in DPBS. Optionally, the CD14+ cells were further purified on a second Percoll gradient. The resultant cells were more than 88% CD14+ and 96% DR+ and less than 3% CD3+, as determined by FACS™ analysis.

Peripheral dendritic cells were separated by Ficoll-hypaque gradient centrifugation. The resultant cells were more than 85% DR+.

Platelets were obtained from heparin-treated whole blood, and washed twice with $Mg^{2+}/Ca^{2+}$-free PBS.

CD4+ or CD8+ T-cell lines or clones were alloactivated as previously described (Rivas et al., *J. Immunol.* 140:2912–18 (1988)) (incorporated by reference for all purposes) by several stimulations with irradiated EBV-transformed B cells. The cells were then cloned by limiting dilution and expanded in IMDM media (Gibco, Grand Island, N.Y.), supplemented with IL-2-containing supernatant from activated PBMC. In some experiments, alloactivated T-cells were separated from feeder cells on Ficoll-Hypaque gradients.

Granulocytes were analyzed directly from whole blood.

B. Immunofluorescence Analysis.

The cell lines described above were tested for their capacity to bind specifically to the P1C5 monoclonal antibody described in Example 1. The existence of specific binding indicates that the cell type expresses a cell surface antigen recognized by the P1C5 antibody. Specific binding was detected either by fluorescently labelling the P1C5 antibody directly or (for granulocytes) by detecting unlabelled P1C5 antibody with a fluorescently labelled goat anti-mouse antibody. An Epics Profile flow cytometer (Coulter Electronics, Hialeah, Fla.) was used for FACS™ analysis. After binding of antibody, cells were incubated in cold PBS solution supplemented with 1% FCS and 0.1% sodium azide. Red blood cells were lysed with 500 μl Optilyse solution (AMAC Inc., Westbrook, Me.) for ten minutes before staining.

TABLE 1

REACTIVITY OF P1C5 mAb

| Cell Subset | |
|---|---|
| PBL's | +/− |
| E+ | +/− |
| CD20+ (B Cells) | − |
| CD56+ (NK Cells) | − |
| CD4+ | − |
| CD4+ (alloantigen activated 7 days) | +/− |
| CD8+ | +/− |
| CD8+ (alloantigen activated 7 days) | ++ |
| CD14+ (monocytes) | ++ |
| Granulocytes | ++ |
| Peripheral Dendritic Cells | ++ |
| PBL's - PHA ACTIVATED (3, 7, 14 DAYS) | +/− |
| PBL's - Con ACTIVATED (3, 7, 14 DAYS) | +/− |
| B-CELL LINES | |
| ARENT, REM, DAUDI, NC37 9037, 9059, 9064, 9062, JY, 721:221, SKF, PGF, KHY MSAB, LBF, CCRF.SB, CESS, RAMOS ST486, JiYOYE, NAMALWA, RAS 1 | +/− − |
| T-CELL LINES MOLT 4, PEER, HPBALL, H178, VB, HSB2 H9, JURKAT, CEM | − |
| ERYTHROID K5622 | +/− |
| MYELOMONOCYTIC KG1a5, HL60, THP1, U937 | − |

++, MCF ≧ 5;
+, 5 > MCF ≧ 3;
+/−, 3 > MCF ≧ 1;
−, MCF < 1.

Table 1 and FIG. 1 show that a high level of expression was consistently observed on alloactivated CD8+ T-cells after 7 days of alloactivation. It was found that the degree of expression increased after successive rounds of alloactivation. By contrast, alloactivated CD4+ T-cells expressed the ARAg-h-1 antigen only after several weeks of alloactivation, and then only weakly and in only a few of the several primary cultures tested. Resting CD8+ T-cells showed weak expression and resting CD4+ T-cells did not express or weakly expressed ARAg-h-1. CD4+ or CD8+ T-cells activated with mitogens such as PHA, PMA, IL-2 or OKT3 did not show expression of ARAg-h-1. Monocytes (CD14+ cells) and granulocytes showed significant expression of ARAg-h-1. Fresh B cells, NK cells and fresh platelets did not express ARAg-h-1. The erythroid cell lines HEL and K562 exhibited weak expression of ARAg-h-1, and myelomonocytic cell lines (HL60, U937, THP1) showed no expression. The vast majority of other EBV-LCL or B cell lines and T-cell lines analyzed did not express ARAg-h-1. Simian (COS-7) or murine (WOP) fibroblastoid cells also did not express ARAg-h-1. These results indicate that ARAg-h-1 is a late activation marker present on alloactivated T-cells (particularly CD8+ cells), monocytes, granulocytes and peripheral dendritic cells.

EXAMPLE 3

Tissue Specificity of P1C5 Monoclonal Antibody

Frozen cryostat sections from normal tissues, including tonsil and thymus, were stained with P1C5 mAb or anti-CD3 antibody. Briefly, acetone-fixed air-dried (4–5 μm) cryostat sections were incubated with P1C5 monoclonal antibody, at room temperature, for 30 min, in a humidified chamber. Sections were transferred serially, interspersed by PBS washes, to Coplin jars containing biotinylated goat anti-mouse IgG (Jackson Immunoresearch, West Grove, Pa.), and incubated with streptavidin-conjugated horseradish peroxidase (Jackson Immunoresearch, West Grove, Pa.), at 4° C., for 30 min. Stains were developed with a 30% solution of 3,3-diaminobenzidine (Sigma Chemical, St. Louis, Mo.) and a 0.3% solution of hydrogen peroxide. Sections were darkened with 0.5% $CuSO_4$ in 1M NaCl, counterstained with 2% methylene blue, dehydrated, and overlaid with a coverslip.

Figure 2A:
FIG. 2: Immunofluorescence micrograph showing presence of ARAg-h-1 in thymus (panels A and B) and tonsil (panels C and D) tissue sections. Tissue sections A and C were stained with a labelled anti-ARAg-h-1 antibody, and sections B and D were stained with a control antibody (anti-CDR3).
Figure 2B:
Figure 2C:
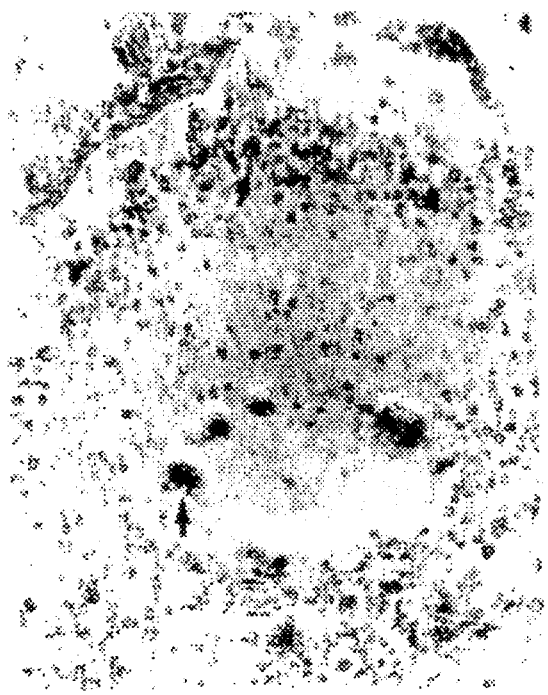
Figure 2D:

From a panel of human tissues, only thymus and tonsil showed staining. FIGS. 2A and 2B show staining of thymic tissue with P1C5 and anti-CD3 antibodies respectively. These Figures indicate that the ARAg antigen is predominantly expressed in medullary thymocytes, particularly in $CD3^+$ medullary thymocytes. A few cortical thymocytes also expressed ARAg-h-1. FIGS. 2C and 2D show staining of the tonsil with P1C5 and anti-CD3 antibodies respectively. This pattern of staining is consistent with the status of ARAg-h-1 as a very late activation marker. In tonsil, the P1C5 mAb preferentially stained a subset of cells located in the T-zone with a weak to moderate intensity (FIG. 2C). Minor subpopulations of cells associated with a dendritic morphology in the epithelium, in the interfollicular T-zones and at the margin of the pale and dark zones of the germinal center also showed strong staining (FIG. 2C). Expression in these subtypes of tonsil cells suggests a possible role for ARAg-h-1 in cell-cell interactions between effector cells and APC/ accessory cell types.

EXAMPLE 4

Selective Inhibition of T-Cell Proliferation by PIC-5 Antibody

P1C5-mediated inhibition of $CD8^+$ and $CD4^+$ T-cell activation was investigated. For alloantigen activation, $CD4^+$ or $CD8^+$ T-cells ($50 \times 10^3 - 100 \times 10^3$) were cultured with $5 \times 10^3$ cells from an irradiated (10 k rads) EBV-transformed LCL cell line (JY), or with irradiated (3 k rads) $CD14^+$ cells ($10 \times 10^3$). The cells were cultured in 200 μl of complete medium in round bottom microtiter wells (EBV-LCL stimulation) or in flat bottom microtiter plates ($CD14^+$ stimulation) in the presence of P1C5 (25 μg/ml) or a control antibody. Cells were cultured in triplicate for 7 days. 1 μCi [3H] TdR (New England Nuclear, Boston, Mass.) was added to each well, and after further culture for 16 hours, cells were harvested with a MASH II apparatus (Microbiological Associates, Walkersville, Md.). For mitogenic stimulation, PBL's, T-cells, $CD4^+$ T-cells or $CD8^+$ T-cells ($1 \times 10^6$/ml) were cultured in 1 μg/ml PHA (Welcome Diagnostics, England) 50 U/ml rIL-2 (Cetus Corp, CA), 40 μg/ml of Con-A (Pharmacia, Uppsala) or 50 ng/ml-anti-CD3 mAb, together with P1C5 (25 μg/ml) or a control antibody

TABLE 2

| MoAb | CD4+ | | CD8+ | | |
|---|---|---|---|---|---|
| | EXP 1 | EXP 2 | EXP 1 | EXP 2 | EXP 3 |
| | | | CPM × 10³ | | |
| NONE | 96 | 98 | 14 | 50 | 73 |
| P1C5 | 135 | 99 | 6 | 27 | 49 |
| α-CD3 | 26 | 11 | 3 | 9 | 2 |
| α-CD4 | 53 | 37 | 13 | 42 | 60 |
| α-CD8 | 100 | nd | 7 | 4 | 23 |

Table 2 shows that the P1C5 mAb specifically inhibited the proliferative response of $CD8^+$ T-cells induced by allotypic EBV-LCL, but did not inhibit the proliferative response of $CD4^+$ T-cells. The P1C5 antibody also inhibited the proliferative response of $CD4^+$ T-cells incubated will allogeneic monocytes (Table 3). The capacity of P1C5 to inhibit $CD4^+$ cell proliferation stimulated by allogeneic monocytes, but not by the JY cell lines, suggests that the target for inhibition is on the monocytes, and not on the $CD4^+$ cells. The P1C5 mAb did not inhibit PHA mitogen-induced proliferation of $CD4^+$ and $CD8^+$ cells (Table 4).

TABLE 3

P1C5 INHIBITION OF THE INTERACTION BETWEEN $CD4^+$ T-CELLS AND MONOCYTES

| mAb ADDED | EXP 1 | EXP 2 |
|---|---|---|
| | CPM | |
| NONE | 18,516 | 28,770 |
| P1C5 | 8,594 (54) | 15,746 (45) |
| CD4 | 1,352 (93) | 3,492 (88) |
| CD8 | 17,008 | 22,170 |

TABLE 4

P1C5 INHIBITION OF PHA STIMULATED $CD4^+$ AND $CD8^+$ T-CELLS

| | CD4+ | | | CD8+ | | |
|---|---|---|---|---|---|---|
| | EXP 1 | EXP 2 | EXP 3 | EXP 1 | EXP 2 | EXP 3 |
| | | | cpm × 10³ | | | |
| NONE | 0.38 | 0.40 | 0.15 | 0.27 | 0.14 | 0.31 |
| PHA + Media | 12.9 | 33.5 | 27.4 | 31.0 | 28.9 | 19.2 |
| PHA + P1C5 | 14.9 | 34.6 | 33.7 | 36.7 | 30.7 | 21.9 |

$CD4^+$ or $CD8^+$ T-cells were activated with PHA (0.5 mg/ml) and P1C5 antibody was added at time zero. Cells were cultured for 3 days before counting incorporated $^3$H-thymidine.

EXAMPLE 5

Effect of PICS Antibody on CTL Activity of $CD8^+$ Cells

The P1C5 antibody was tested for capacity to inhibit the cytotoxicity of alloactivated $CD8^+$ T-cell lines by the procedure of Rivas et al., J. Immunol. 142:1840–46 (1989) (incorporated by reference for all purposes). Briefly, the T-cells were incubated with P1C5 or a control antibody for 45 min. $2 \times 10^3$ $^{51}$Cr-labelled target cells (JY) were added in a total volume of 200 μl in a microtiter well. The mixture was incubated for 4 hours at 37° C. Radioactivity released by the target cells was measured.

TABLE 5

EFFECT OF P1C5 mAb ON CTL ACTIVITY

| mAb added (25 mg/μl) | EXP 1 | | | EXP 2 | | |
|---|---|---|---|---|---|---|
| | 75:1 | 50:1 | E:T RATIO 25:1 | 75:1 | 50:1 | 25:1 |
| | | | % cytotoxicity | | | |
| NONE | 56 | 51 | 48 | 56 | 44 | 48 |
| P1C5 | 67 | 57 | 40 | 49 | 50 | 45 |
| CD3 | 5 | 1 | 1 | 13 | 13 | 3 |
| CD4 | 55 | 48 | 43 | 54 | 56 | 27 |

Table 5 shows that P1C5 mAb had no effect on the cytotoxicity mediated by $CD8^+$ CTL. By contrast, anti-CD3 mAb inhibited the specific lysis of the target cells. These results show that although P1C5 monoclonal antibody blocks the alloantigen-mediated activation of $CD8^+$ T-cells, it does not block the cytolytic activity of these cells when added after proliferation.

EXAMPLE 6

Isolation of Antigen (ARAg-h-1) Recognized by P1C5

Monocytes, prepared as in Example 2, were washed three times with cold PBS at 4° C., followed by addition of 50 μl of lactoperoxidase (Sigma, St Louis, Mo.), 500 μCi of $^{125}I$, 20 μl of 30% H202, diluted twice at 1:5000, at 5 min intervals at 4° C. The radiolabelled cells were washed three times with PBS at 4° C. and lysed with 2% Triton-X 100 in PBS containing 0.1% $NAN_3$, 1 mM PMSF, 1 μg/ml Aprotinin, 2 μg/ml Leupeptin and 1 μg/ml Pepstatin, as protease inhibitors (Boehringer, Mannheim, West Germany). The cell lysates were centrifuged at 13,000 g for 15 min. at 4° C. and insoluble material discarded. The radiolabelled cell extract was precleared with Zysorbin-G (Zymed, San Francisco, Calif.) either with or without normal rabbit serum (Jackson Immunoresearch, West Grove, Pa.) for 30 min. at 4° C. The precleared lysate was centrifuged and immunoprecipitated using P1C5 antibody conjugated to Protein-G (Zymed, San Francisco, Calif.) incubated for 16 to 18 h. under agitation at 4° C. Nonspecifically-bound radiolabelled proteins were removed by layering lysates over 600 μl of lysis buffer (25 mM Tris-HCL (pH 7.5), 5 mM EDTA (pH 7.5), 250 mM NaCl, 1% Triton X-100) containing 0.25M sucrose and microcentrifuging for 3 min at 13,000 g. The pellet was washed with 1 ml lysis buffer supplemented with 2M urea and incubated for 2 min at room temperature. After aspiration of the urea-sucrose solution, the protein G-sepharose beads were washed five times in lysis buffer. The samples were boiled for 3 min in 70 μl SDS-PAGE buffer containing of 5% 2-mercaptoethanol to elute bound radiolabeled protein. Samples were analyzed on 6% SDS PAGE gels. Gels were stained with Coomassie blue and dried. The radioactive bands were visualized by fluorography at −70° C.

Figure 3:
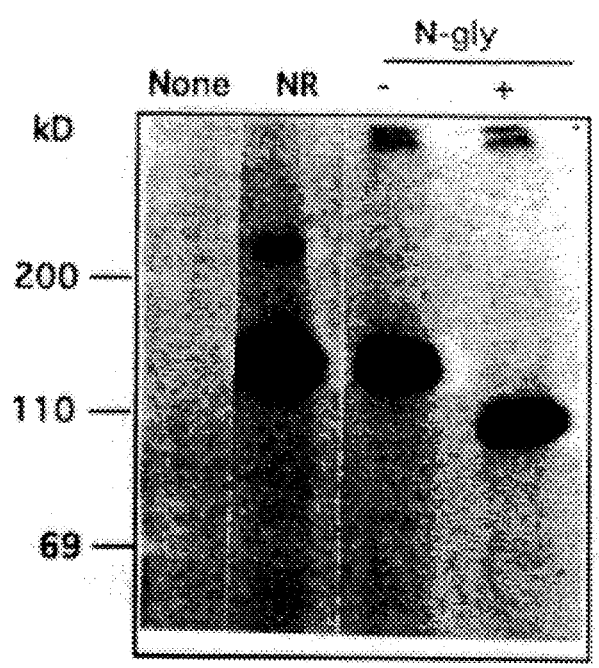
FIG. 3: SDS-PAGE analysis showing expression of ARAg-h-1 on monocytes before and after treatment with N-glycanase.

FIG. 3 (Track 2) shows that the major band precipitated by P1C5 has a molecular weight of about 135 kDa. A minor band of about 218 kDa appeared to be co-precipitated in some gels but disappeared on extensive washing, and is probably artifactual. Similar results were obtained when the above procedure was repeated using alloactivated $CD8^+$ T-cells in place of monocytes.

The protein immunoprecipitated by P1C5 was analyzed for the presence of carbohydrate residues. A P1C5 immunoprecipitate was boiled at 100° C. for 10 min in 5 μl buffered 5% SDS, 10% B-ME. Six μl 10% NP-40, 7 μl reaction buffer (pH 7.5) and 5 μl PNGase F or Endo-H (Bio Labs, New England) were added. The samples were incubated at 37° C. for 60 min, resuspended in 50 μl of sample buffer, and analyzed by SDS-PAGE. FIG. 3 (track 4) shows that N-glycanase treatment shifted the major protein band from 135 kDa to 110 kDa, indicating that ARAg-h-1 is a glycoprotein containing Asn-linked carbohydrate side chains.

EXAMPLE 7

Cloning DNA encoding ARAg-h-1

A cDNA clone encoding the ARAg gene was isolated by the general approach of Seed et al., Proc. Natl. Acad. Sci. USA 84:3365 (1987) (incorporated by reference for all purposes). Briefly, mRNA was isolated from a noncytolytic regulatory $CD8^+$ human T-cell clone related to the CS1 immunogen by which P1C5 was derived, and which expressed the ARAg-h-1 antigen at relatively high density on its surface. The mRNA was used to generate an oligo (dT)-primed cDNA library. After elimination of inserts less than 1.5 kb, the library was ligated to nonself-complementary BstXI adaptors and inserted into a derivative of the plasmid pcDNA I (Invitrogen, Inc., San Diego, Calif.) according to the manufacturer's instructions. The resulting cDNA library, containing about $5 \times 10^5$ independent clones, was introduced into COS-7 cells via electroporation in a Gene Pulser (BioRad Corp., Richmond, Calif.) set at 350 V, 400 ohms, 960 μFd, and time constants of about 12 mS. Cells expressing ARAg-h-1 were enriched by three rounds of immunoselection using the P1C5 mAb.

This procedure identified a single cDNA plasmid clone containing a 3.3 kb insert that directed cell-surface expression of ARAg-h-1 in transfected COS-7 cells.

EXAMPLE 8

Expression of the ARAg-h-1 Clone
A. Northern Analysis of ARAg-h-1 mRNA

Figure 4:
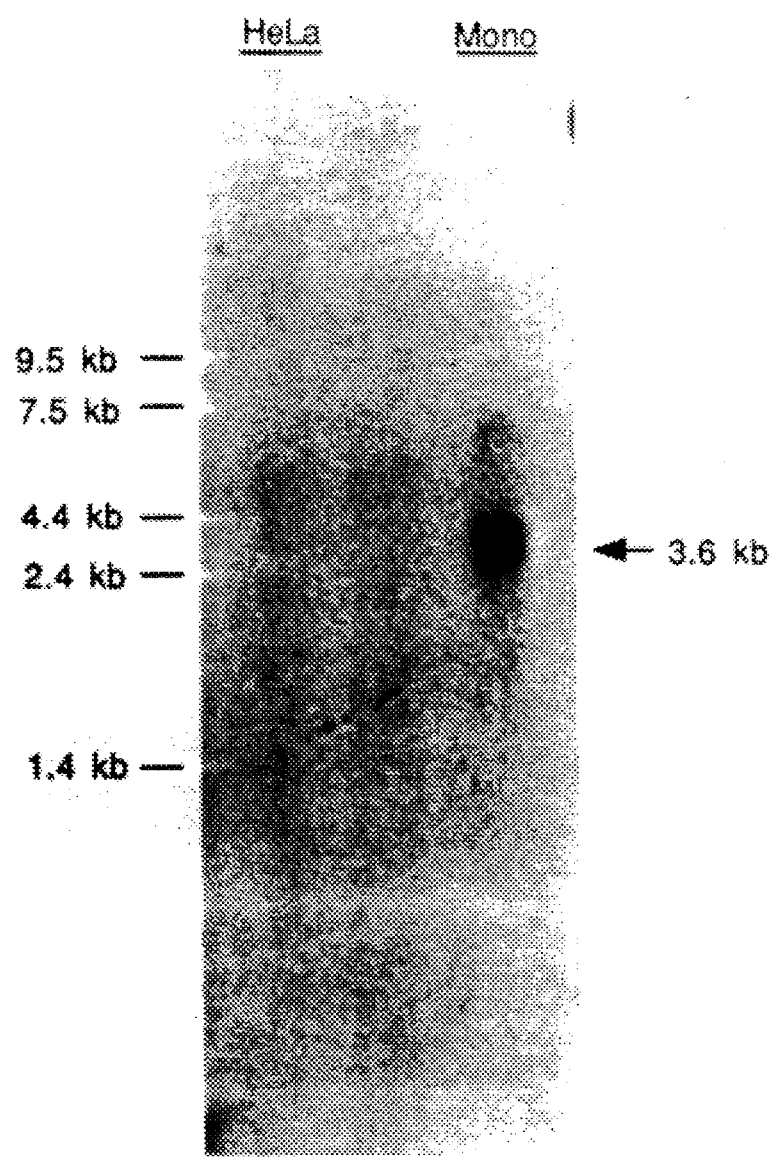
FIG. 4: Northern blot showing expression of ARAg-h-1 in monocytes compared with a HeLa cell control.
Figure 5:
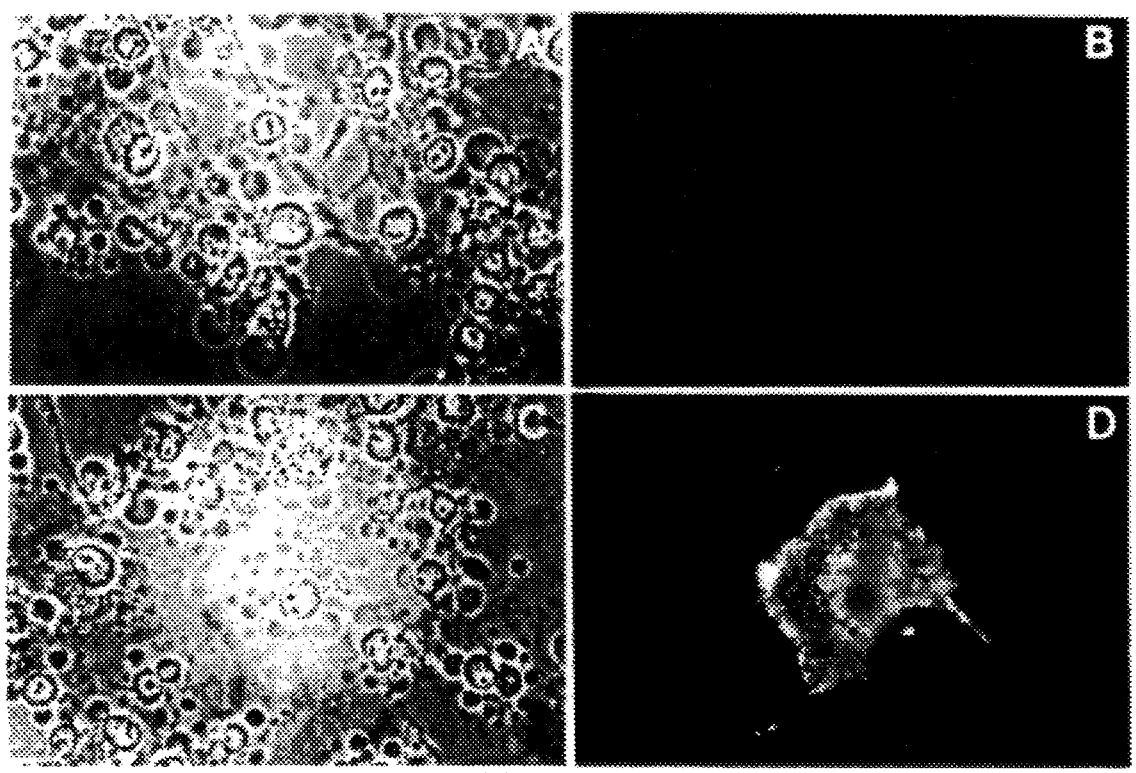
FIG. 5: Micrographs showing expression of ARAg in transfected COS-7 cells. Panels C and D are phase contrast and fluorescence micrographs of COS-7 cells transfected with a vector encoding ARAg-h-1. Panels A and B are controls showing COS-7 cells transfected with unmodified vector.

The size of native ARAg mRNA transcripts was determined by purifying $poly(A)^+$ mRNA from fresh human monocytes, fractionating mRNA on a denaturing agarose gel, transferring the mRNA to a nylon membrane and hybridizing with a $^{32}P$-labeled DNA probe spanning bases 1–2038 of the ARAg-h-1 sequence shown in FIG. 7A. FIG. 4 shows a single major band of about 3.6 kb in monocyte mRNA. The band was absent in a HeLa cell control. A minor band at 6.4 kb may represent an incompletely spliced transcript. The major 3.6 kb mRNA is only slightly larger than the 3.34 kb cDNA insert identified in Example 7. The small difference in molecular weight indicates that only short stretches of the extreme 5', and or 3', termini of the mRNA are missing from the cDNA clone of the ARAg gene.
B. Immunofluorescence of ARAg-h-1 antigen expressed by transfected COS-7 cells COS-7 cells transfected with ARAg-h-1 cDNA plasmid by electroporation (see Example 7) were cultured for 24 hr. The cells were detached with trypsin, and allowed to adhere to glass microscope coverslips. After culturing for an additional 24 hr, live cells were incubated with P1C5 mAb for 30 min, washed five times with PBS, and incubated with rabbit-anti-mouse IgG conjugated with Texas Red (Jackson ImmunoResearch Laboratories, Inc., West Grove, Pa.). The cells were washed as above and examined with a Zeiss fluorescent microscope (Carl Zeiss, Inc., Thornwood, N.Y.). FIG. 5 shows that the transfected cells expressed ARAg-h-1 as a cell surface antigen (panels A and B). The antigen was not expressed on control cells transfected with unmodified vectors (panels C and D).

C. Immunoprecipitation

Figure 6:
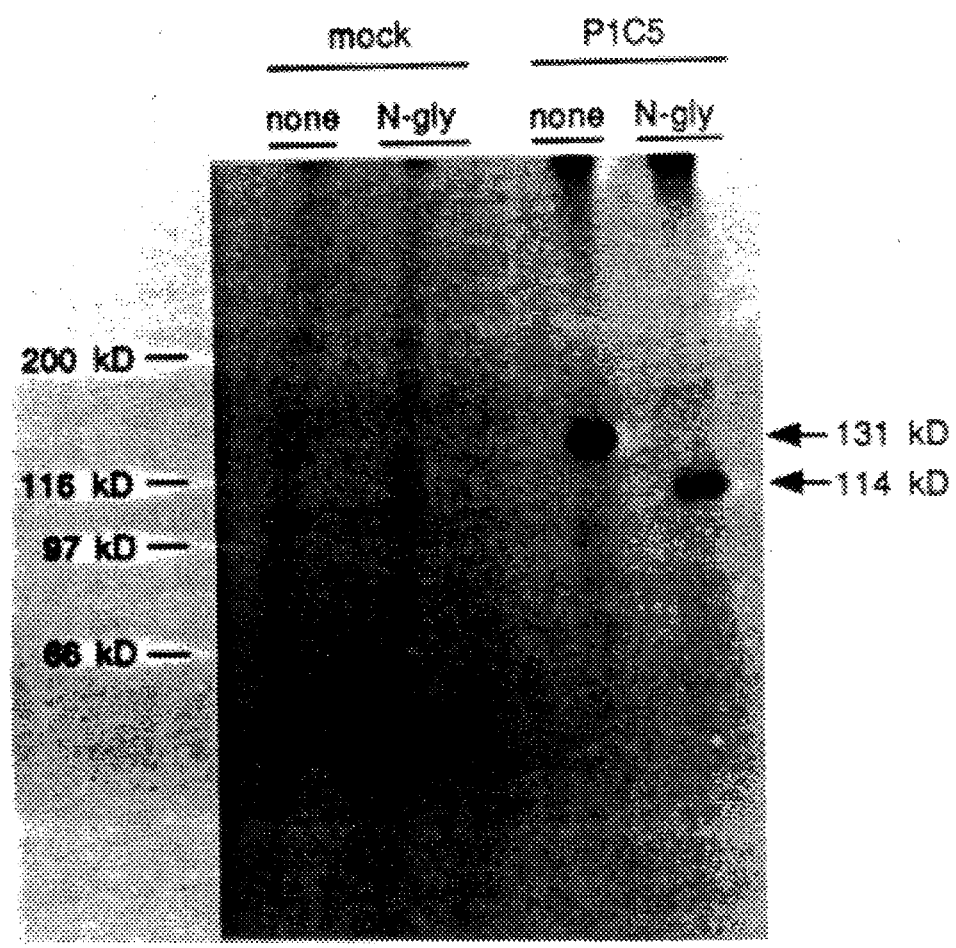
FIG. 6: SDS-PAGE analysis of ARAg-h-1 protein immunoprecipitated from transfected COS-7 cells with and without N-glycanase treatment.

The ARAg-h-1 cDNA plasmid was transfected into WOP cells (Dailey et al., *J. Virol.* 54:739 (1985) (a murine 3T3 cell line transformed by the polyoma virus T antigen), and cultured for 48 hr. Cell surface proteins were labelled with iodine-125 using lactoperoxidase. Proteins were extracted with detergent and precipitated with the P1C5 antibody. FIG. 6 shows that P1C5 monoclonal antibody specifically precipitated a 131 kDa protein, indistinguishable from that immunoprecipitated from alloactivated $CD8^+$ cells and monocytes. FIG. 6 also shows that N-glycanase treatment reduces the molecular weight of the labelled band from 131 kDa to 114 kDa, as was observed for the band immunoprecipitated from alloactivated $CD8^+$ cells and monocytes.

EXAMPLE 9

Sequence Analysis of ARAg-h-1

Both strands of the ARAg-h-1 cDNA insert and subclones thereof were sequenced by the Sanger method (Sanger et al., *Proc. Natl. Acad. Sci. USA* 74:5463 (1977)), using Sequenase (U.S. Biochemical Inc., Cleveland, Ohio). Sequences were analyzed using the Intelligenetics Suite program (Intelligenetics, Inc., Mountain View, Calif.) and the GCG program (University of Wisconsin Genetics Computer Group, Madison, Wis.) (Devereux et al., *Nucleic Acid Res.* 12:387 (1984) (incorporated by reference for all purposes).

FIG. 7A shows that the ARAg-h-1 cDNA clone contains a 3,340 bp insert consisting of a 21 bp 5'-untranslated region, a 3,063 bp open-reading frame (1,021 amino acids) and a 256 bp 3'-untranslated region. The AUG translation initiation codon of the predicted open reading frame conforms partially to the Kozak consensus in which the +4 base is guanosine and the −3 position is free of a purine (Kozak et al., *Nucleic Acids Res.* 15:8125 (1987) (incorporated by reference for all purposes). However, this is most likely the true initiator site for this particular extended open reading frame because an in-frame stop codon exists 18 bp upstream of the other putative AUG initiator in question. Initiation from a suboptimal signal sequence is consistent with the relatively low levels of ARAg that are found on the surface of activated T lymphocytes, monocytes and granulocytes. The cDNA clone lacks a poly(A) tail, which may have been lost in the course of shuttling between procaryotic and eucaryotic hosts in the isolation process.

The predicted ARAg-h-1 peptide sequence reveals hydrophobic stretches at the $NH_2$-terminus and near the COOH-terminus (FIG. 7B). The $NH_2$-terminal hydrophobic stretch terminates with a signal sequence consensus cleavage site (von Heijne, *Eur. J. Biochem.* 133:17 (1983); von Heijne, *Nucleic Acids Res.* 14:4683 (1986) (each of which is incorporated by reference for all purposes) between Gly-20 and Gln-21. The single additional hydrophobic stretch spanning residues 955–979 is probably a transmembrane domain. Accordingly, mature ARAg-h-1 is a type I integral membrane protein having a 934-residue extracellular $NH_2$-terminal domain and a short highly charged 42-residue cytoplasmic COOH-terminal domain. The ARAg-h-1 extracellular domain contains seven potential Asn-linked glycosylation sites (Asn-Xaa-Ser/Thr) (Bairoch, *Nucleic Acids Res.* 20:2013 (1992)) (incorporated by reference for all purposes). The 42 amino acids cytoplasmic domain contains 20 charged amino acids and shows no substantial sequence identity to any other known protein. The cytoplasmic domain contains several potential phosphorylation sites (protein kinase C, residues 986, 991 and 1,009; casein kinase II, residue 991; and cAMP-dependent kinase residue 982). Phosphorylation may transduce signals responsive to binding of ARAg-h-1- to a receptor. The predicted molecular size of the 1,001-residue mature polypeptide is 112,935 kDa, in excellent agreement with the observed molecular weight of ARAg-h-1 after deglycosylation. The 17 kDa shift in molecular weight on deglycosylation from about 131 kDa to 114 kDa is consistent with the derivatization of all seven predicted Asn-linked glycosylation sites with oligosaccharide chains of about 2.5 kDa average size.

Nucleic and protein sequences for ARAg-h-1 were compared with data base sequences using the BLAST program (Altschul et al., *J. Mol. Biol.* 215:403 (1990); Karlin et al., *Proc. Natl. Acad. Sci. USA* 87:2264 (1990)) and the BLAZE programs (Smith et al., *J. Mol. Biol.* 147:195 (1981)) (each of which is incorporated by reference for all purposes). The ARAg-h-1 nucleotide sequence showed no substantial sequence identity with any sequence in the data bases Genbank Release 76 and EMBL Release 34. The ARAg-h-1 amino acids sequence showed a low degree of sequence identity (15–20%) with several IgSF members. The highest degree of sequence identity was observed with a heparin sulfate proteoglycan (Kallunki et al, *J. Cell Biol* 116:559 (1992); Murdoch et al., *J. Biol. Chem.* 267:8544 (1992), an IgSF member containing 22 Ig-like domains which scored 6.0 S.D.'s above the mean. Other proteins exhibiting relatively high degrees of identity included the Drosophila adhesion molecules neuroglian (5.0 S.D.'s) (Bieber et al., *Cell* 59:447 (1989)), fasciclin (4.4 S.D.'s) (Grenningloh et al., *Cold Spring Harbor Symp. Quant. Biol.* 55:323 (1990)), and macrophage colony stimulating factor receptor (4.5 S.D.'s) (Coussens et al., *Nature* 320:277 (1986)), all of which are IgSF members.

The sequence similarity between ARAg-h-1 and some known IgSF members, and the regularity of spacing between cysteine residues throughout the predicted extracellular domain of ARAg-h-1, suggest that the ARAg-h-1 extracellular domain comprises seven disulfide-linked Ig loops from 73 to 81 amino acids in length. Of the three types of Ig domains known (V, C1 and C2), the lengths of the ARAg-h-1 loops are most consistent with the variable, or V-type, domains (Williams et al., *Ann. Rev. Immunol.* 6:381 (1988) (incorporated by reference for all purposes). Alignment of the seven putative ARAg Ig domains (FIG. 8) revealed a striking conservation of residues critical to Ig V-domain folding (Williams, supra), particularly disulfide-forming cysteine residues, internal Trp and Arg residues and a Asp-Xaa-Gly-Xaa-Tyr-Xaa-Cys (SEQ. ID NO: 1) motif at the COOH-terminal end of the domains.

TABLE 6

| Statistical Analysis of ARAg-h-1 Ig-like Domains | | | | | | | |
|---|---|---|---|---|---|---|---|
| | V1 | V2 | V3 | V4 | V5 | V6 | V7 |
| V-type | | | | | | | |
| TCRβ V | 0.0 | 2.0 | 1.2 | 1.7 | 2.0 | 1.2 | 4.3 |
| TCRγ V | 4.5 | 3.8 | 0.0 | 1.4 | 0.8 | 5.7 | 5.4 |
| TCRδ V | 0.0 | 0.3 | 5.5 | 1.9 | 0.1 | 1.7 | 6.0 |
| $P_0$ v | 2.7 | 3.8 | 2.5 | 2.3 | 2.8 | 2.1 | 2.2 |
| Amalgam V | 2.2 | 4.9 | 4.8 | 6.3 | 3.3 | 4.6 | 4.7 |
| pIgR V1 | 1.7 | 3.1 | 3.4 | 4.0 | 0.9 | 0.6 | 3.4 |
| pIgR V2 | 3.8 | 3.6 | 1.3 | 1.3 | 0.5 | 2.8 | 3.8 |
| pIgR V3 | 2.8 | 1.1 | 2.0 | 2.5 | 0.7 | 0.4 | 1.9 |
| pIgR V4 | 1.5 | 3.5 | 2.8 | 0.1 | 0.9 | 0.3 | 3.0 |
| CD8 V | 2.6 | 3.2 | 2.8 | 0.6 | 0.0 | 2.0 | 4.4 |

TABLE 6-continued

Statistical Analysis of ARAg-h-1 Ig-like Domains

|  | V1 | V2 | V3 | V4 | V5 | V6 | V7 |
|---|---|---|---|---|---|---|---|
| CD4 V | 3.1 | 4.3 | 2.2 | 4.0 | 1.1 | 2.4 | 3.0 |
| Igκ V | 4.6 | 2.9 | 0.8 | 2.5 | 0.3 | 0.8 | 3.4 |
| Igλ V | 5.0 | 2.4 | 1.6 | 0.0 | 0.0 | 2.4 | 1.9 |
| IgH V | 0.9 | 1.7 | 4.5 | 3.4 | 2.4 | 1.3 | 2.5 |
| C2-type |  |  |  |  |  |  |  |
| CEA C5 | 2.5 | 2.6 | 2.5 | 2.2 | 2.0 | 0.9 | 0.0 |
| CEA C6 | 0.0 | 2.5 | 1.1 | 0.3 | 0.0 | 1.4 | 0.4 |
| NCAM C4 | 3.0 | 2.6 | 0.2 | 2.7 | 0.0 | 0.0 | 4.6 |
| PDGF-R C3 | 0.7 | 0.0 | 0.2 | 3.3 | 0.6 | 0.8 | 1.4 |
| MAG C4 | 3.0 | 2.2 | 3.7 | 3.1 | 0.0 | 1.3 | 3.2 |
| FcR$_{G1/2b}$ C1 | 1.6 | 0.9 | 1.5 | 3.4 | 1.4 | 3.5 | 0.6 |
| FcR$_{G1/2b}$ C2 | 0.3 | 0.4 | 1.6 | 2.2 | 0.8 | 0.0 | 0.2 |
| C1-type |  |  |  |  |  |  |  |
| IgG HC1 | 0.9 | 0.3 | 0.0 | 1.7 | 4.3 | 0.8 | 1.4 |
| IgG HC2 | 1.4 | 1.5 | 3.6 | 0.9 | 0.9 | 3.1 | 1.5 |
| IgC HC3 | 0.3 | 0.2 | 0.3 | 0.3 | 3.6 | 0.3 | 1.2 |
| TCRβ c | 0.4 | 0.7 | 1.6 | 0.5 | 0.7 | 0.5 | 0.7 |

The table lists the Needleman-Wunsch alignment scores (100 randomizations) in units of S.D. for comparison of the seven ARAg V-type Ig domains (V1 to V7) with selected representatives from the families of known V-type, C1-type and C2-type Ig domains. Scores of 3.1, 4.3 and 5.2 indicate chance probabilities of $10^{-3}$, $10^{-5}$ and $10^{-7}$, respectively (Williams, supra). Alignment scores ≧3.0 are shown in boldface.

The assignment of the ARAg-h-1 Ig domains to the V-type category was confirmed by statistical comparison of the ARAg-h-1 domains to prototypic domains of the three different Ig domain types. Table 6 summarizes the results of alignments expressed as the number of S.D.'s by which the alignment score exceeds the mean of alignment scores for randomly shuffled versions of the sequences being tested (Williams, supra). S.D. values of 3.1, 4.3 and 5.1 correspond to probabilities of $10^{-3}$, $10^{-5}$ and $10^{-7}$, respectively, of a coincidental match (Williams, supra). All of the ARAg Ig domains (with the exception of the fifth domain) scored highest against representative members of the V-type Ig domain family (Table 6). Notable V-type domains that show some similarity with ARAg domains include those residing in the TCR γ-chain, TCR δ-chain, the poly-Ig receptor and CD4. Matches of ARAg-h-1 domains with C1 and C2 Ig domain categories were less frequent and usually the matching of any one domain was inconsistent with matching of other domains. Overall, 14% and 18% of the entries for the C1 and C2 categories of Ig domain, respectively, resulted in alignment scores ≧3.0, whereas 35% of alignment scores for V-type regions were ≧3.0. Furthermore, 18% of V-type scores were ≧4.0 whereas only 3% of C-type scores were ≧4.0. The V-type Ig gene superfamily member exhibiting the best fit to the ARAg V-type domains is the amalgam protein, an IgSF member expressed by Drosophila (Seeger et al., Cell 55:589 (1988). The schematic representation of the predicted Ig domain structure and cell surface topology of ARAg-h-1 is summarized in FIG. 9.

TABLE 7

Intramolecular Relationship of ARAg Ig-like Domains

|  | V2 | V3 | V4 | V5 | V6 | V7 |
|---|---|---|---|---|---|---|
| V1 | 6.7 | 5.7 | 2.7 | 0.5 | 2.7 | 4.3 |
| V2 | — | 9.8 | 7.2 | 0.0 | 7.2 | 6.7 |
| V3 | — | — | 5.1 | 0.6 | 10.4 | 6.1 |
| V4 | — | — | — | 3.5 | 4.8 | 5.1 |
| V5 | — | — | — | — | 6.0 | 4.1 |
| V6 | — | — | — | — | — | 7.2 |
| V7 | — | — | — | — | — | — |

The values listed are the alignment scores in units of standard deviations.

The seven Ig V-type domains (V-1 through V-7) of ARAg-h-1 have also been compared for sequence similarity with each other. V-3 is most closely related to V-2 and V-6; V-1 and V-4 are closer to V-2 and V-3 than V-6, and V-7 is closer to V-6 than to the other V domains. (Table 7). V-5 is somewhat related to V-4, V-6 and V-7, but not to V-1, V-2 and V-3. V-5 matched only one other V-type domain with a score of greater than 3.0, this being the amalgam V-type domain.

The amino acid similarity of ARAg to other IgSF members suggests a role for ARAg in cell-surface recognition events. Such interactions may include homotypic or heterotypic cell-cell adhesion as well as binding to one or more soluble molecules.

The above examples are provided to illustrate the invention but not to limit its scope. Other variants of the invention will be readily apparent to one of ordinary skill and are encompassed by the claims of the invention. All publications, patents and patent applications cited in the application are hereby incorporated by reference for all purposes to the same extent as if each were individually denoted as being incorporated by reference.

What is claimed is:

1. A purified alloreaction-associated antigen (ARAg) polypeptide comprising at least 20 contiguous amino acids from the amino acid sequence shown in FIG. 7A (SEQ. ID No. 3) and having an antigenic determinant common to a protein comprising the amino acid sequence shown in FIG. 7A.

2. The polypeptide of claim 1 that is encoded by a nucleic acid segment having 80% sequence identity to a nucleic acid fragment having the nucleotide sequence shown in FIG. 7A (SEQ. No. 2).

3. The polypeptide of claim 2 that comprises an extracellular domain.

4. The polypeptide of claim 3, wherein said extracellular domain comprises an immunoglobulin-like domain.

5. The polypeptide of claim 4, wherein said extracellular domain comprises seven immunoglobulin-like domains.

6. The polypeptide of claim 5, wherein said domains are variable-type domains.

7. The polypeptide of claim 6 that has a molecular weight of about 131 kDa before treatment with N-glycanase and about 114 kDa thereafter.

8. The polypeptide of claim 7, wherein said polypeptide is present on the surface of alloantigen-activated CD8$^+$ T-cells, monocytes, granulocytes and peripheral dendritic cells, and is substantially absent on resting T-cells and mitogen-activated CD8$^+$ T-cells, B-cells, erythroid cell lines, myelomonocitic cell lines, EBV-LCL cell lines or fibroblastoid cell lines.

9. The polypeptide of claim 8 that is naturally occurring.

10. The polypeptide of claim 9 that is human.

11. The purified alloreaction-associated polypeptide ARAg-h-1 having the amino acid sequence shown in FIG. 7A (Seq. ID. No. 3).

12. An extracellular domain of alloreaction-associated antigen ARAg-h-1, wherein said ARAg-h-1 has the amino acid sequence shown in FIG. 7A (SEQ ID NO: 3), and wherein said extracellular domain is a fragment of said ARAg-h-1 comprising an immunoglobulin-like domain.

13. The extracellular domain of claim 12, comprising seven variable-type immunoglobulin domains.

14. The extracellular domain of claim 13 that is a full-length extracellular domain.

* * * * *